United States Patent
Dolezal et al.

(10) Patent No.: US 7,279,482 B2
(45) Date of Patent: Oct. 9, 2007

(54) HETEROCYCLIC COMPOUND BASED ON $N^6$-SUBSTITUTED ADENINE, METHODS, OF THEIR PREPARATION, THEIR USE FOR PREPARATION OF DRUGS, COSMETIC PREPARATIONS AND GROWTH REGULATORS, PHARMACEUTICAL PREPARATIONS, COSMETIC PREPARATIONS AND GROWTH REGULATORS CONTAINING THESE COMPOUNDS

(75) Inventors: Karel Dolezal, Vidce (CZ); Igor Popa, Olomouc (CZ); Jan Holub, Olomouc (CZ); René Lenobel, Stemberk (CZ); Stefaan Werbrouck, Harelbeke (BE); Miroslav Strnad, Olomouc (CZ); Marek Zatloukal, Sumperk (CZ)

(73) Assignee: Ústav experimentální botaniky Akademie ved České republiky, Prague (CZ)

( * ) Notice: Subject to any disclaimer, the term of this patent is extended or adjusted under 35 U.S.C. 154(b) by 132 days.

(21) Appl. No.: 10/485,091

(22) PCT Filed: Aug. 1, 2002

(86) PCT No.: PCT/CZ02/00045

§ 371 (c)(1),
(2), (4) Date: Sep. 7, 2004

(87) PCT Pub. No.: WO03/040144

PCT Pub. Date: May 15, 2003

(65) Prior Publication Data

US 2005/0043328 A1    Feb. 24, 2005

(30) Foreign Application Priority Data

Aug. 2, 2001  (CZ) .................. 2001-2818

(51) Int. Cl.
  C07D 473/34  (2006.01)
  A61K 31/52  (2006.01)
  A61P 37/06  (2006.01)
  A61P 35/00  (2006.01)
  A01N 43/54  (2006.01)

(52) U.S. Cl. .................. 514/263.4; 544/277; 504/136

(58) Field of Classification Search .............. 544/277; 514/263.4

See application file for complete search history.

(56) References Cited

U.S. PATENT DOCUMENTS

| | | | | |
|---|---|---|---|---|
| 2,956,998 A | * | 10/1960 | Baizer et al. | 544/277 |
| 3,041,340 A | * | 6/1962 | Bullock et al. | 544/277 |
| 3,213,095 A | * | 10/1965 | Bambury et al. | 544/277 |
| 3,321,293 A | * | 5/1967 | Sousa | 504/168 |
| 5,164,394 A | * | 11/1992 | Bolund et al. | 514/263.23 |
| 5,371,089 A | * | 12/1994 | Rattan | 514/263.23 |
| 5,656,264 A | * | 8/1997 | Hanada et al. | 424/70.1 |
| 6,498,163 B1 | * | 12/2002 | Boschelli et al. | 514/264.1 |
| 2006/0166295 A1 | * | 7/2006 | Woods et al. | 435/7.92 |

FOREIGN PATENT DOCUMENTS

| | | | |
|---|---|---|---|
| JP | 07233037 A | * | 9/1995 |
| WO | WO 0149688 A1 | * | 7/2001 |

OTHER PUBLICATIONS

Vaňková, Journal of Chromatography A, vol. 811, Issues 1-2, Jun. 19, 1998, pp. 77-84.*
Vesely, et al., European Journal of Biochemistry, vol. 224, 771-786, 1994.*
Translation of JP 07-233037.*
Translation of JP 07-233037 (1995).*

* cited by examiner

Primary Examiner—Mark L. Berch
(74) Attorney, Agent, or Firm—Notaro & Michalos P.C.

(57) ABSTRACT

Heterocyclic derivatives based on $N^6$-substituted adenine of, e.g., a formula:

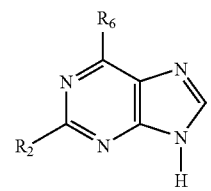

wherein R2 is hydrogen, R6 is R6'-X, X is —NH—, and R6' is substituted phenyl or substituted benzyl. The derivatives possess anticancer, mitotic, imunosuppressive and antisenescent properties for plant, animal and human cells, and methods of their preparation are disclosed. Included are also pharmaceutical compositions, cosmetic preparations and growth regulators, which contain these derivatives as active compound and the use of these derivatives for the preparation of drugs, cosmetic preparations, in biotechnological processes, in cosmetics and in agriculture.

6 Claims, 10 Drawing Sheets

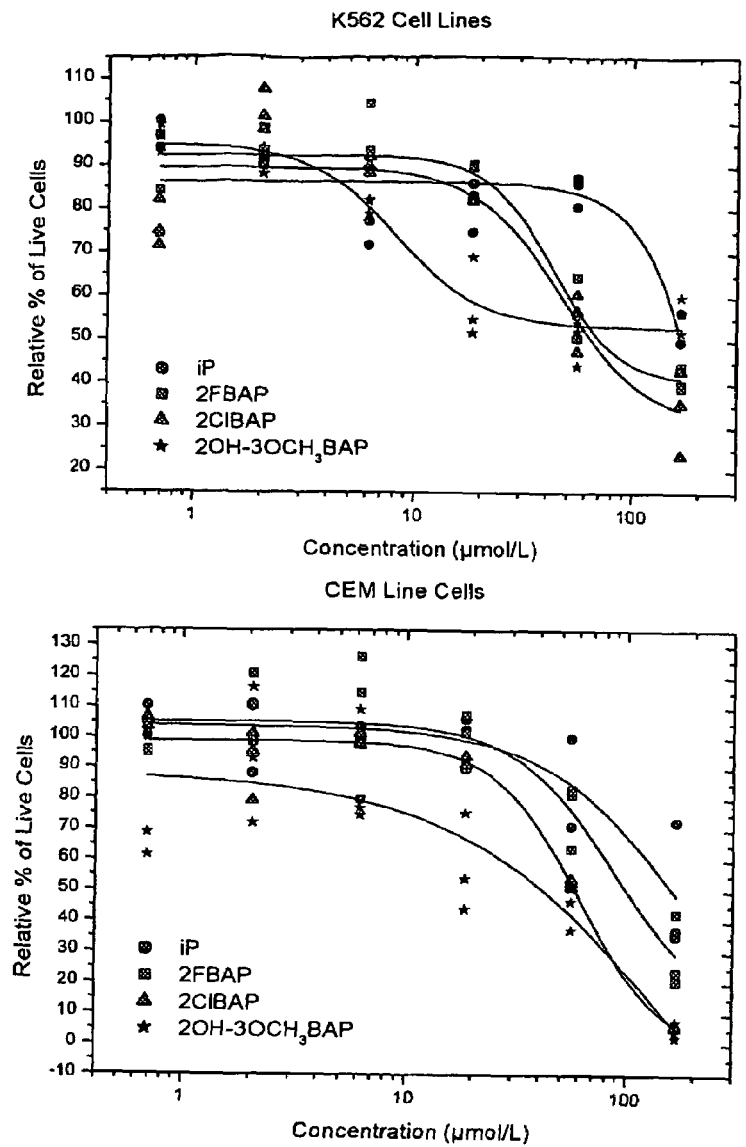

Figure 1: Inhibition of growth of K562 (A) and CEM (B) tumour cell lines by tested compounds. Cytotoxicity was determined in the presence of Calcein AM. Activity is presented as percentage of maximal activity (in the absence of inhibitors). iP: isopentenyladenine; 2F BAP: 6-(2-fluorobenzylamino)purine; 2Cl BAP: 6-(2-chlorobenzylamino)purine; 2OH-3OCH$_3$ BAP: 6-(2-hydroxy-3-methoxybenzylamino)purine.

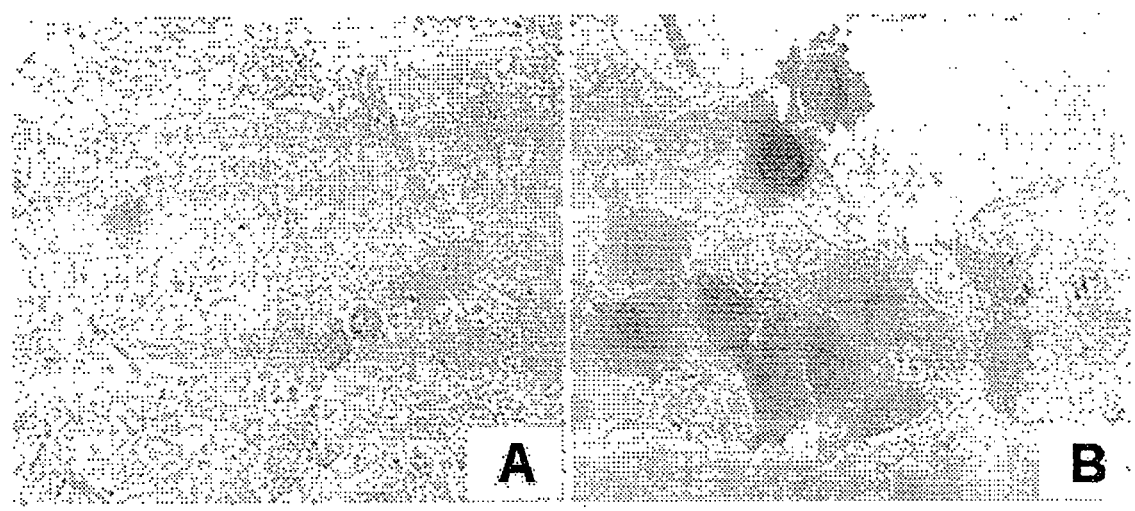
Figure 2: Senescent Cells in Culture of Human Fibroblasts (B) (the other cells (A)) stained blue due to the action of β-galactosidase on the substrate X-gal (5-bromo-4-chloro-3-indolyl-β-D-galactopyranosid) (1 mg/ml).

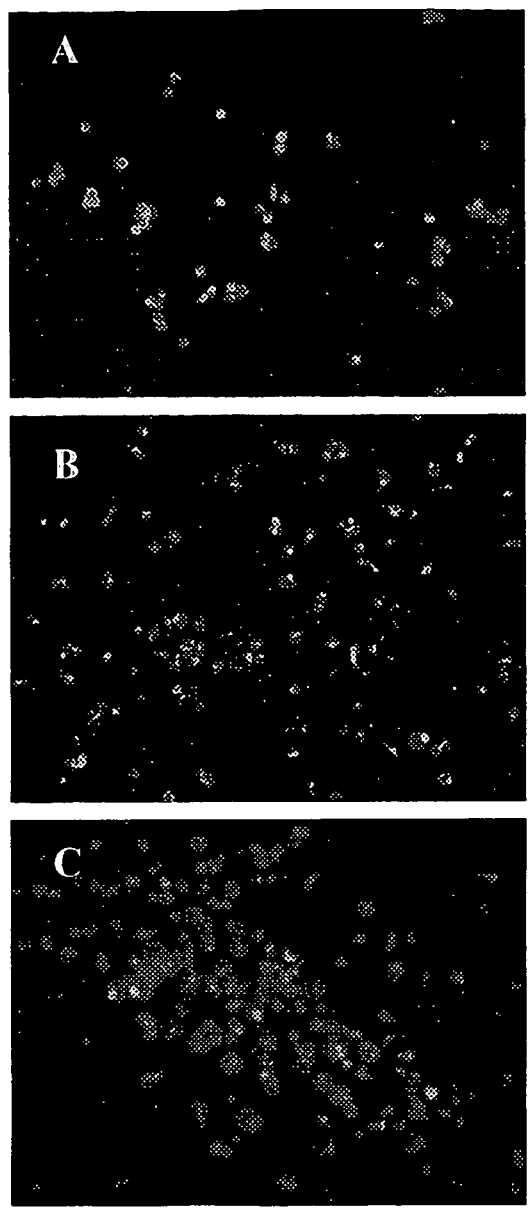
Figure 3: Induced Apoptosis in Tumour Cells MCF-7 cell line after application of cytokinin 6-(2-hydroxy-3-methoxybenzylamino)purine. A MCF-7, apoptotic cells: 6 h, 12, 20µM, B MCF-7, secondary necrotic cells (i.e. necrosis following apoptosis), 12 h, 12, 40 µM; C MCF-7, necrotic cells, 24h, 12, 40µM. Anexin FITC V (Mol. Probes) and propidium iodide staining: anexin – green, PI – red.

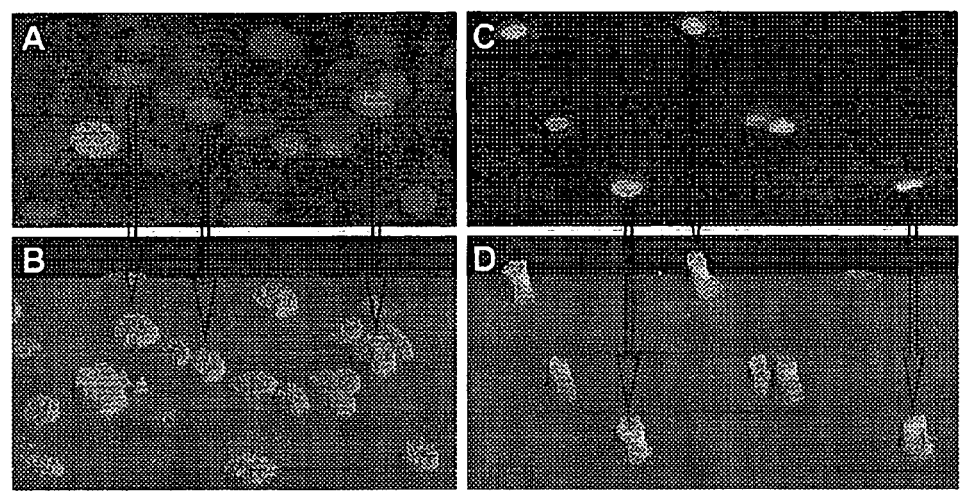

Figure 4: Apoptotic cells detection using Anexin (green fluorescence) and Hoechstem 33285 (blue fluorescence) staining. Analysed using "Olympus image analysis" after treatment of MCF-7 tumour cells by 6-(2-hydroxy-3-methoxybenzylamino)purine. A,B – control cells without treatment; C,D – apoptotic cells (condensation of chromatin); A,C – fluorescence microscopy; B,D –fluorescence image analysis.

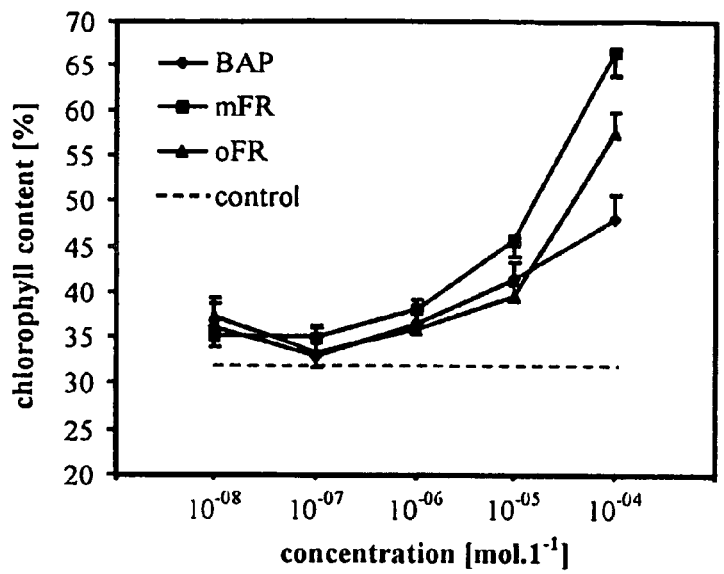
Figure 5: Effect of tested compounds on retention of chlorophyll in excised wheat leaf tips. Values are expressed as % of initial chlorophyll content of fresh leaves before the incubation. Error bars show standard deviations of the mean for 5 replicate determinations. Dashed line indicates control incubation without any cytokinin, which was 31,7 ± 0,9.

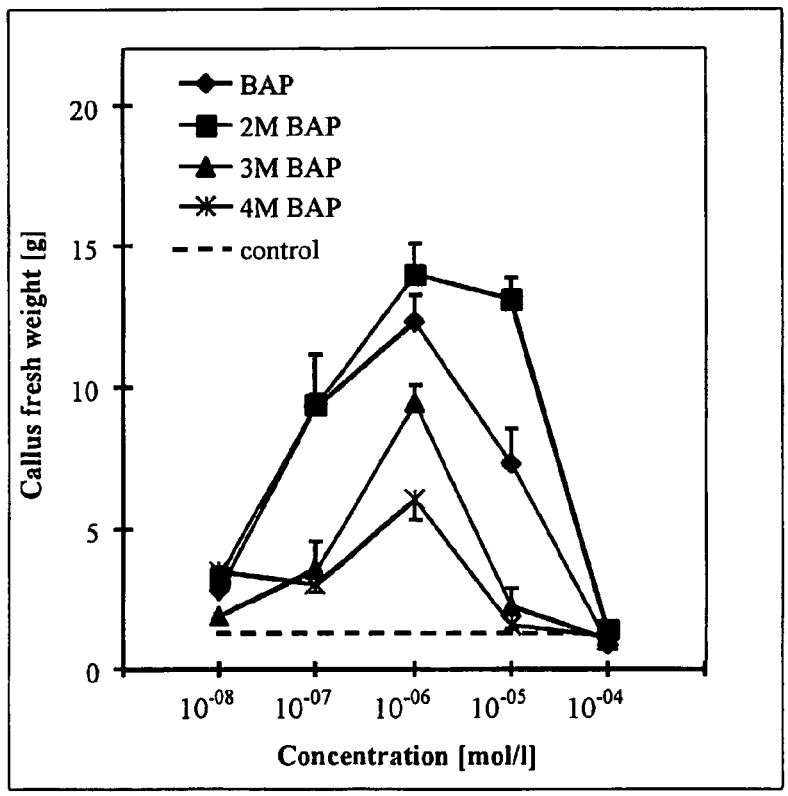
Figure 6: Effect of tested compounds on fresh weight yield of tobacco callus culture. Error bars show standard deviations of the mean for 5 replicate determinations. Dashed line indicates the value for the control treatment without any cytokinin, 2,2 ± 0,4 g.

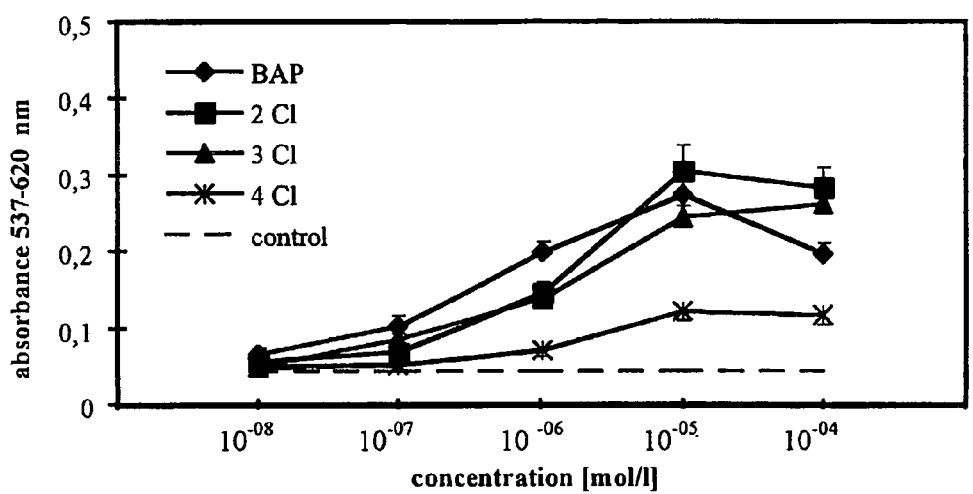

Figure 7: Effect of tested compounds on dark induction of betacyanin synthesis in *Amaranthus caudatus* cotyledon/hypocotyl explants. Error bars show standard deviations of the mean for 5 replicate determinations. Dashed line indicates the values for the control treatment without added cytokinin, 0.043±0.009. Values represent the difference in O.D. units between absorption at 537 and 620 nm.

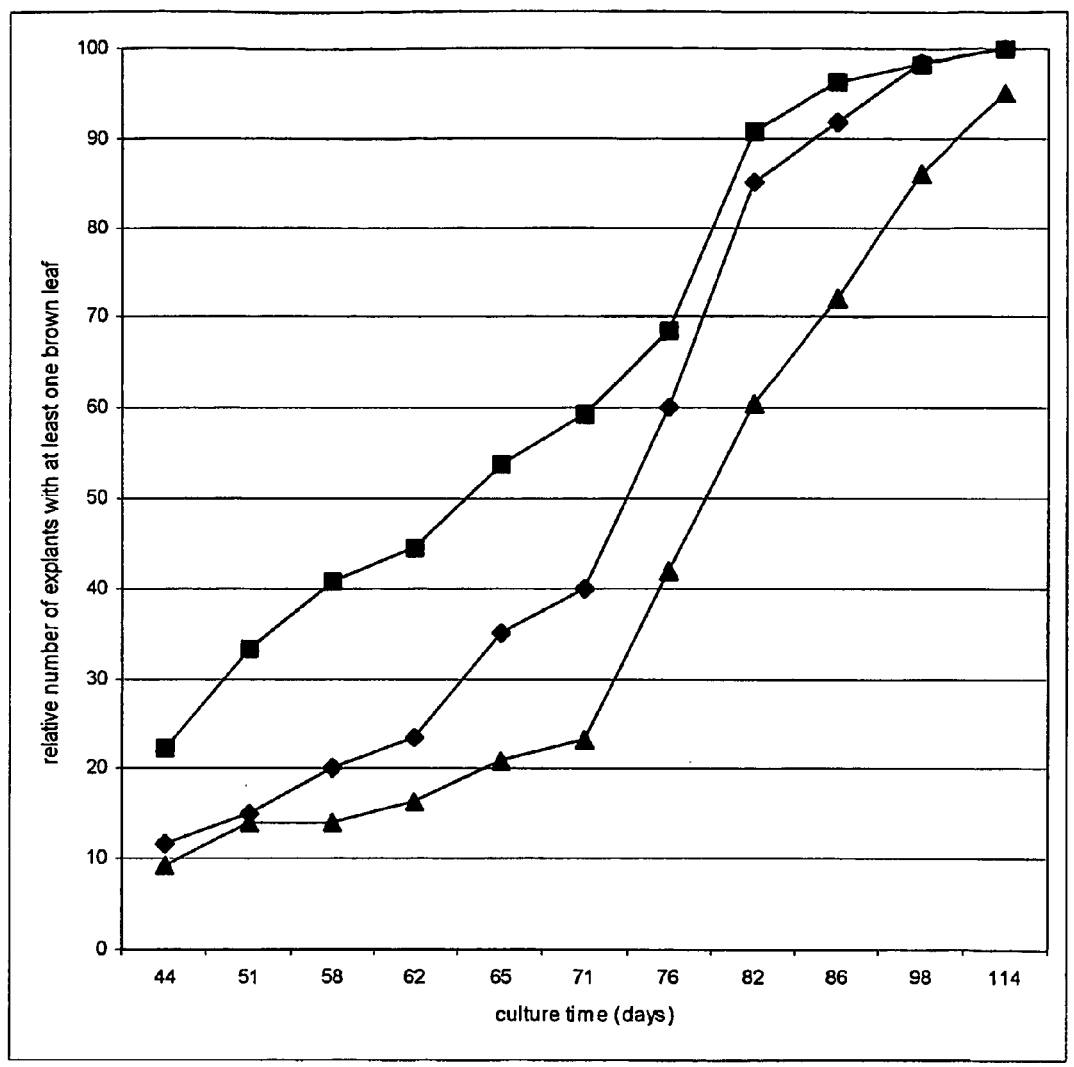
Fig. 8. Relative number of explants with at least one brown leaf in function of culture time
(■: BA, ●: mT, ▲: mMeOBAP)

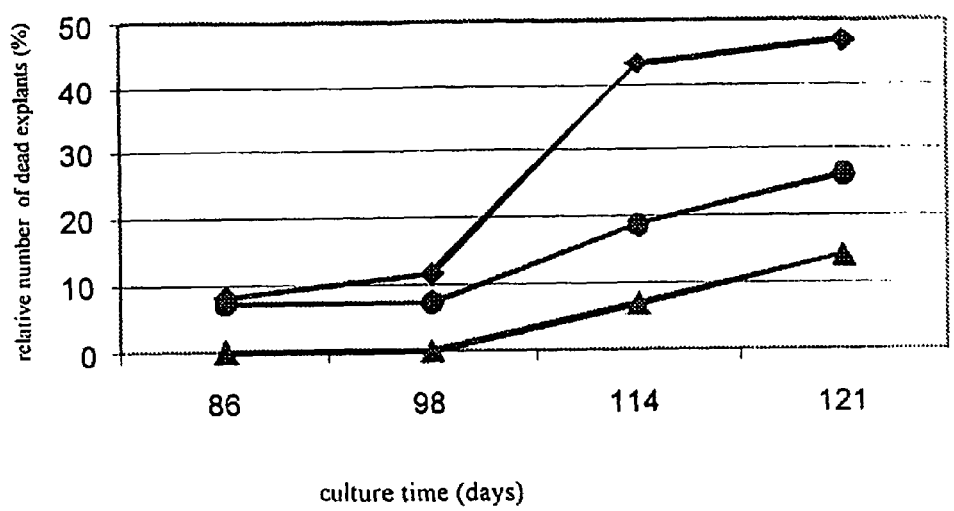
Fig. 9. Relative number of dead explants in relation to culture time (■: BA, ●: mT, ▲: mMeOBAP).

Fig 10. Left: dead *Rosa* explant on BA containing medium; right: vigorous *rosa* plantlet after 121 days cultivation on mMeOBAP containing medium

HETEROCYCLIC COMPOUND BASED ON N⁶-SUBSTITUTED ADENINE, METHODS, OF THEIR PREPARATION, THEIR USE FOR PREPARATION OF DRUGS, COSMETIC PREPARATIONS AND GROWTH REGULATORS, PHARMACEUTICAL PREPARATIONS, COSMETIC PREPARATIONS AND GROWTH REGULATORS CONTAINING THESE COMPOUNDS

TECHNICAL FIELD

The invention relates to new heterocyclic derivatives based on N⁶-substituted adenine, having anticancer, mitotic, imunosuppressive and antisenescent properties for plant, animal and human cells, methods of their preparation and their use as drugs, pharmaceutical compositions, which contain these derivatives as active compound and the use of these derivatives for the preparation of drugs, cosmetic preparations, in biotechnological processes, in cosmetics and in agriculture.

BACKGROUND ART

Well proven plant regulatory compounds are phytohormones. An important place among them have cytokinins. Structurally, all naturally occurring cytokinins belong to the homogenous group of N⁶-substituted adenine derivatives, playing an important role in many different developmental processes, including cell division, growth and differentiation, as well as flower and fruit development. They can break seed dormancy, inhibit apical dominance and stimulate the growth of side shoots, delay the cell ageing, increase stress resistance, affect cell membrane permeability and cause accumulation of various metabolites in the site of their application (Letham a Palni 1983—Ann. Rev. Plant. Physiol. 34: 163-197, 1983, Mok, D. W. S., Mok, M. C.: Cytokinins: Chemistry, Activity and Function. CRC Press, Boca Raton, London, Tokyo 1994).

Their interaction with auxins is especially important in stimulation of cell division and regulation of cell differentiation in plant tissue cultures (Skoog, Miller 1957). The general definition of cytokinins as group of plant growth regulators is also based on this effect (Skoog, F., Armstrong, D. J.: Cytokinins.—Ann. Rev. Plant Physiol. 21: 359-384, 1970). 6-benzylaminopurin (BAP), together with kinetin, is usually used as an active cytokinin for plant in vitro cultures. This compound was for long time thought to be purely synthetic, however, its natural occurrence in plants was recently proved. There are usually refereed as a cytokinins also a compounds having limited or none biological activity (7- and 9-glucosides, amino acid conjugates, some hyper modified cytokinins in tRNA). From this reason, compounds structurally derived from N⁶-substituted adenine are refereed as cytokinins also in this application.

Since all living organisms on the Earth have been evolutionary developing together for many millions of years, the presence of regulatory interactions of plant compounds, as cytokinins are, in animals and human can be assumed. Cytokinin-derived compounds probably affect many different molecular mechanisms in animal and human cells. We recently discovered, that novel generations of anti-inflammatory, anticancer, immunosuppressive, antiviral and other drugs could be based on N⁶-substituted purines and their derivatives.

The aim of this invention to provide anticancer, immunosuppressive, growth-regulatory, morphogenetically active and antisenescence heterocyclic compounds having improved selectivity and efficiency index, i.e. that are less toxic yet more efficacious than analogues known heretofore.

DISCLOSURE OF INVENTION

Object of this invention are heterocyclic compounds based on N⁶-substituted adenine of the general formula I adenine have formula I

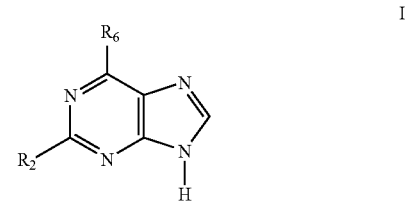

and the pharmaceutically acceptable salts thereof, wherein
R2 is hydrogen, halogen, hydroxy, alkoxy, amino, hydrazo, mercapto, methylmercapto, carboxyl, cyano, nitro, amido, sulfo, sulfamido, acylamino, acyloxy, alkylamino, dialkylamino, alkylmercapto, cycloalkyl and carbamoyl group,
R6 is alkyl, substituted alkyl, cycloalkyl, substituted cycloalkyl, cycloalkylalkyl, arylalkyl, heteroalkyl, heteroarylalkyl, cycloheteroalkyl alkyl or
R6'-X, wherein
X is —O—, —S—, —NH—, —N(C1-6 alkyl)-;
R6' is hydrogen, alkyl, substituted alkyl, acyl, cycloalkyl, substituted cycloalkyl, aryl, substituted aryl, heterocycle, heteroaryl, substituted heteroaryl, arylalkyl, cycloheteroalkyl, substituted cycloheteroalkyl, heteroarytalkyl, heteroalkyl, cycloalkyl alkyl, cycloheteroalkyl, amido and sulfo;
whereas the generic substituent groups have meanings identical with the definitions of the corresponding groups as defined in this legend, wherein
"halogen" refers to fluorine, bromine, chlorine and iodine atoms;
"hydroxy" refers to the group —OH;
"mercapto" refers to group —SH;
"alkyl" refers to branched or unbranched $C_1$-$C_6$ chain which is saturated or unsaturated being selected from the groups such as methyl, propyl, isopropyl, tert-butyl, allyl, vinyl, ethinyl, propargyl, hexen-2-yl and the like exemplifying this term;
"substituted alkyl" refers to alkyl as just described including one to five substituents such as hydroxyl, mercapto, alkylmercapto, halogen, alkoxy, acyloxy, amino, acylamino, hydrazino, carbamoyl, amido, carboxyl, sulfo, acyl, guanidino and the like, whereby these groups may be attached to any carbon atom of the alkyl moiety;
"alkoxy" denotes the group —OR, where R is alkyl, substituted alkyl, aryl, substituted aryl, arylalkyl, substituted arylalkyl, cycloalkyl, substituted cycloalkyl, cycloheteroalkyl or substituted cycloheteroalkyl as defined herein;
"alkylmercapto" denotes the group —SR, where R is as defined for "alkoxy" group;
"sulfo" denotes the group —$SO_3R$, where R is H, alkyl or substituted alkyl as defined herein;
"sulfamido" denotes to the group $SO_2NRR''$ where R and R'' is H, alkyl or substituted alkyl;

"acyl" denotes groups —C(O)R, where R is hydrogen, alkyl, substituted alkyl, aryl, substituted aryl, arylalkyl, substituted arylalkyl, cycloalkyl, substituted cycloalkyl as defined herein;

"aryloxy" denotes groups —OAr, where Ar is an aryl, substituted aryl, heteroaryl or substituted heteroaryl group as defined herein.

"alkylamino" denotes the group —NRR', where R and R' may independently be hydrogen, alkyl, substituted alkyl, aryl, substituted aryl, heteroaryl or substituted heteroaryl as defined herein;

"camido" denotes the group —C(O)NRR', where R and R' may independently be hydrogen, alkyl, substituted alkyl, aryl, substituted aryl, heteroaryl, substituted heteroaryl as defined herein;

"carboxyl" denotes the group —C(O)OR, where R is hydrogen, alkyl, substituted alkyl, aryl, substituted aryl, hetaryl or substituted hetaryl as defined herein;

"acylamino" denotes the group —NHCOR, where R may be alkyl, substituted alkyl, heterocycle, aryl, substituted aryl, heteroaryl and substituted heteroaryl as defined herein;

"carbamoylamino" denotes the group NHCOOR, where R is alkyl or aryl;

"aryl" or "ar" refers to an aromatic carbocyclic group having at least one aromatic ring as phenyl or biphenyl or multiple condensed rings in which at least one ring is aromatic as 1,2,3,4-tetrahydronaphthyl, naphthyl, anthryl, or phenanthryl;

"substituted aryl" refers to aryl as just described which is optionally substituted with one to five functional groups such as halogen, alkyl, hydroxy, amino, acylamino, carbamoylamino, hydrazino, mercapto, alkoxy, alkylmercapto, alkylamino, amido, carboxyl, nitro, sulfo as defined herein;

"heterocycle" refers to an unsaturated or aromatic carbocyclic group having at least one hetero atom, such as N, O or S, within the ring; the ring being single such as pyranyl, pyridyl or furyl or multiple condensed such as quinazolinyl, purinyl, quinolinyl or benzofuranyl which can optionally be unsubstituted or substituted with halogen, amino, hydroxy, cyano, nitro, mercapto, alkoxy, alkylamino, acylamino, carbamoylamino, acyloxy, dialkylamino, alkylmercapto, carboxyl, amido, sulfo, sulfamido, and the like as defined;

"heteroaryl" refers to a heterocycle in which at least one heterocyclic ring is aromatic;

"substituted heteroaryl" refers to a heterocycle optionally mono or poly substituted with one to five functional groups, such as halogen, amino, hydroxy, cyano, nitro, mercapto, alkoxy, alkylamino, acylamino, carbamoylamino, acyloxy, dialkylamino, alkylmercapto, carboxyl, amido, sulfo, sulfamido, and the like as defined;

"arylalkyl" refers to the group —R—Ar where Ar is an aryl group and R is alkyl or substituted alkyl group wherein the aryl groups can optionally be unsubstituted or substituted with groups such as halogen, amino, acylamino, carbamoylamino, hydrazino, acyloxy, alkyl, hydroxyl, alkoxy, alkylmercapto, alkylamino, amido, carboxyl, hydroxy, aryl, nitro, mercapto, sulfo and the like as defined herein;

"heteroalkyl" refers to the group —R-Het where Het is a heterocycle group and R is an alkyl group, said heteroalkyl groups being optionally unsubstituted or substituted with groups such as halogen, amino, hydroxy, cyano, nitro, mercapto, alkoxy, alkylamino, acylamino, carbamoylamino, acyloxy, dialkylamino, alkylmercapto, carboxyl, amido, sulfo, sulfamido, and the like as defined herein before;

"heteroarylalkyl" refers to the group —R-Het-Ar where HetAr is a heteroaryl group and R is alkyl or substituted alkyl whereas the heteroarylalkyl groups can optionally be unsubstituted or substituted with the groups such as halogen, alkyl, substituted alkyl, alkoxy, alkylmercapto, nitro, thiol, sulfo and the like as defined herein before;

"cycloalkyl" refers to a divalent cyclic or polycyclic alkyl group containing 3 to 15 carbon atoms;

"substituted cycloalkyl" refers to a cycloalkyl group comprising one to five substituents from the group consisting of halogen, amino, hydroxy, cyano, nitro, mercapto, alkoxy, alkylamino, acylamino, carbamoylamino, acyloxy, dialkylamino, alkylmercapto, carboxyl, amido, sulfo, sulfamido, and the like as defined herein before;

"cycloheteroalkyl" refers to a cycloalkyl group as defined wherein at least one of the ring methylene group is replaced with a group selected from the groups NH, OH, SH;

"substituted cycloheteroalkyl" refers to a cycloheteroalkyl group as herein defined which contains one to five substituents, such as halogen, amino, hydroxy, cyano, nitro, mercapto, alkoxy, alkylamino, acylamino, carbamoylamino, acyloxy, dialkylamino, alkylmercapto, carboxyl, amido, sulfo, sulfamido and the like as defined herein before;

"cycloalkyl alkyl" denotes the group —R-cycloalkyl where cycloalkyl is a cycloalkyl group and R is an alkyl or substituted alkyl wherein the cycloalkyl groups can optionally be unsubstituted or substituted with halogen, amino, hydroxy, cyano, nitro, mercapto, alkoxy, alkylamino, acylamino, carbamoylamino, acyloxy, dialkylamino, alkylmercapto, carboxyl, amido, sulfo, sulfamido and the like as defined herein;

"cycloheteroalkyl alkyl" denotes he group —R-cycloheteroalkyl where R is an alkyl or substituted alkyl wherein the cycloheteroalkyl groups can optionally be unsubstituted or substituted with halogen, amino, hydroxy, cyano, nitro, mercapto, alkoxy, alkylamino, acylamino, carbamoylamino, acyloxy, dialkylamino, alkylmercapto, carboxyl, amido, sulfo, sulfamido and the like as defined herein before and the racemates, optical isomers and acid salts thereof The following derivatives are particularly preferred, namely: 6-(2-hydroxy-3-chloroxybenzylamino)purine, 6-(2-hydroxy-4-chlorobenzylamino)purine, 6-(2-hydroxy-5-chlorobenzylamino)purine, 6-(2-hydroxy-6-chlorobenzylamino)purine, 6-(2-hydroxy-3-iodobenzylamino)purine, 6-(2-hydroxy-4-iodobenzylamino)purine, 6-(2-hydroxy-5-iodobenzylamino)purine, 6-(2-hydroxy-6-iodobenzylamino)purine, 6-(2-hydroxy-3-bromobenzylamino)purine, 6-(2-hydroxy-4-bromobenzylamino)purine, 6-(2-hydroxy-5-bromobenzylamino)purine, 6-(2-hydroxy-6-bromobenzylamino)purine, 6-(2-hydroxy-3-fluorobenzylamino)purine, 6-(2-hydroxy-4-fluorobenzylamino)purine, 6-(2-hydroxy-5-fluorobenzylamino)purine, 6-(2-hydroxy-6-fluorobenzylamino)purine, 6-(2,3-dihydroxy-4-methoxybenzylamino)purine, 6-(2,5-dihydroxy-4-methoxybenzylamino)purine, 6-(2,6-dihydroxy-3-methoxybenzylamino)purine, 6-(2,3-dihydroxy-3-methoxybenzylamino)purine, 6-(2,5-dihydroxy-3-methoxybenzylamino)purine, 6-(2,6-dihydroxy-4-methoxybenzylamino)purine, 6-(2,3-dihydroxy-4-chlorobenzylamino)purine, 6-(2,3-dihydroxy-4-chlorobenzylamino)purine, 6-(2,5-dihydroxy-4- chlorobenzylamino)purine, 6-(2,6-dihydroxy-4-chlorobenzylamino)purine, 6-(2,6-dihydroxy-4-bromoxybenzylamino)purine, 6-(2,6-dihydroxy-4-iodobenzylamino)purine, 6-(2,6-dihydroxy-3-chlorobenzylamino)purine, 6-(2,6-dihydroxy-3-bromobenzylamino)purine, 6-(2,6-dihydroxy-3-iodobenzylamino)purine, 6-(2,6-dihydroxy-3-fluorobenzylamino)purine, 6-(2,6-dihydroxy-3,5-dichlorobenzylamino)purine, 6-(2,6-dihydroxy-3,5-dibromobenzylamino)purine, 6-(2,6-dihydroxy-3,5-diiodobenzylamino)purine, 6-(2,6-dihydroxy-3,5-difluorobenzylamino)purine, 6-(2-fluorobenzylamino)purine, 6-(3-fluorobenzylamino)purine, 6-(4-fluorobenzylamino)purine, 6-(2-bromobenzylamino)purine, 6-(3-bromobenzylamino)purine, 6-(4-bromobenzylamino)purine, 6-(2-iodobenzylamino)purine, 6-(3-iodobenzylamino)purine, 6-(4-iodobenzylamino)purine, 6-(2-chlorobenzylamino)purine, 6-(2-chlorobenzylamino)purine, 6-(3-chlorobenzylamino)purine, 6-(4-chlorobenzylamino)purine, 6-(2-acetylbenzylamino)purine, 6-(3-acetylbenzylamino)purine, 6-(4-acetylbenzylamino)purine, 6-(3-karboxybenzylamino)purine, 6-(4-karboxybenzylamino)purine, 6-(2-acetoxybenzylamino)purine, 6-(3-acetoxybenzylamino)purine, 6-(4-acetoxybenzylamino)purine, 6-(2-nitrobenzylamino)purine, 6-(3-nitrobenzylamino)purine, 6-(4-nitrobenzylamino)purine, 6-(2-sulfobenzylamino)purine, 6-(3-sulfoobenzylamino)purine, 6-(4-sulfobenzylamino)purine, 6-(2-kyanobenzylamino)purine, 6-(3-kyanobenzylamino)purine, 6-(4-kyanobenzylamino)purine, 6-(5-nitro-2-methylbenzylamino)purine, 6-(2-methylbenzylamino)purine, 6-(3-methylbenzylamino)purine, 6-(4-methylbenzylamino)purine, 6-(4-methylaminobenzylamino)purine, 6-(2-methoxybenzylamino)purine, 6-(3-methoxybenzylamino)purine, 6-(4-methoxybenzylamino)purine, 6-(2-hydroxybenzylamino)purine, 6-(3-hydroxybenzylamino)purine, 6-(4-hydroxybenzylamino)purine, 6-(4-hexylbenzylamino)purine, 6-(4-hexyloxybenzylarnino)purine, 6-(2-formylbenzylamino)purine, 6-(3-formylbenzylamino)purine, 6-(4-formylbenzylamino)purine, 6-(2-ethoxybenzylamino)purine, 6-(3-ethoxybenzylamino)purine, 6-(4-ethoxybenzylamino)purine, 6-(4-ethylbenzylamino)purine, 6-(4-penthylbenzylamino)purine, 6-(4-penthyloxybenzylamino)purine, 6-(4-fenoxybenzylamino)purine, 6-(4-fenylbenzylamino)purine, 6-(4-propylbenzylamino)purine, 6-(4-propyloxybenzylamino)purine, 6-(4-oktylbenzylamino)purine, 6-(4-octyloxybenzylamino)purine, 6-(4-ethyloxybenzylamino)purine, 6-(3,4-diacetoxybenzylamino)purine, 6-(3,5-diacetoxybenzylamino)purine, 6-(2,5-diaminobenzylamino)purine, 6-(3,5-dibromobenzylamino)purine, 6-(3,5-dibromo-4-methoxybenzylamino)purine, 6-(2,3-dichlorobenzylamino)purine, 6-(2,4-dichlorobenzylamino)purine, 6-(2,5-dichlorobenzylamino)purine, 6-(2,6-dichlorobenzylamino)purine, 6-(3,4-dichlorobenzylamino)purine, 6-(3,5-dichlorobenzylamino)purine, 6-(2,3,4,5-tetrafluorobenzylamino)purine, 6-(2-chloro-3,6-difluorobenzylamino)purine, 6-(5-chloro-2-fluorobenzylamino)purine, 6-(2,3,4-trifluorobenzylamino)purine, 6-(2,3,5-trifluorobenzylamino)purine, 6-(2,4,5-trifluorobenzylamino)purine, 6-(3,4,5-trifluorobenzylamino)purine, 6-(2,3,6-trifluorobenzylamino)purine, 6-(3-chloro-2,6-difluorobenzylamino)purine, 6-(2-chloro-6-fluorobenzylamino)purine, 6-(2,6-difluorobenzylamino)purine, 6-(2,4-difluorobenzylamino)purine, 6-(3,4-difluorobenzylamino)purine, 6-(2,5-difluorobenzylamino)purine, 6-(3,5-difluorobenzylamino)purine, 6-(5-fluoro-2-(trifluoromethyl)benzylamino)purine, 6-(4-fluoro-2-(trifluoromethyl)benzylamino)purine, 6-(2-chloro-5-(trifluoromethyl)benzylamino)purine, 6-(2-(difluoromethoxy)benzylamino)purine, 6-(3-(difluoromethoxy)benzylamino)purine, 6-(4-(difluoromethoxy)benzylamino)purine, 6-(2-fluoro-5-(trifluoromethyl)benzylamino)purine, 6-(3-fluoro-4-(trifluoromethyl)benzylamino)purine, 6-(2-fluoro-4-(trifluoromethyl)benzylamino)purine, 6-(2-(trifluoromethylthio)benzylamino)purine, 6-(2-fluoro-3-(trifluoromethyl)benzylamino)purine, 6-(2-chloro-6-fluoro-3-methylbenzylamino)purine, 6-(6-chloro-2-fluoro-3-methylbenzylamino)purine, 6-(3-chloro-2-fluoro-5-(trifluoromethyl)benzylamino)purine, 6-(3-chloro-2-fluoro-6-(trifluoromethyl)benzylamino)purine, 6-(2,3-difluoro-4-methylbenzylamino)purine, 6-(2,6-difluoro-3-methylbenzylamino)purine, 6-(2-fluoro-6-(trifluoromethyl)benzylamino)purine, 6-(3-chloro-2,6-difluorobenzylamino)purine, 6-(3-(trifluoromethylthio)benzylamino)purine, 6-(3-fluoro-4-methyl benzylamino)purine, 6-(4-fluoro-3-methylbenzylamino)purine, 6-(5-fluoro-2-methylbenzylamino)purine, 6-(2-chloro-3,6-difluorobenzylamino)purine, 6-(4-(trifluoromethylthio)benzylamino)purine, 6-(3-fluoro-5-(trifluoromethyl)benzylamino)purine, 6-(2-chloro-4-fluorobenzylamino)purine, 6-(2-(trifluoromethoxy)benzylamino)purine, 6-(3-(trifluoromethyl)benzylamino)purine, 6-(2-(trifluoromethyl)benzylamino)purine, 6-(4-(trifluoromethyl)benzylamino)purine, 6-(4-chloro-3-(trifluoromethyl)benzylamino)purine, 6-(4-fluoro-3-(trifluoromethyl)benzylamino)purine, 6-(3,5-bis(trifluoromethyl)benzylamino)purine, 6-(3-(trifluoromethoxy)benzylamino)purine, 6-(4-(trifluoromethoxy)benzylamino)purine, 6-(4-(trifluoromethyl)benzylamino)purine, 6-(4-diethylaminobenzylamino)purine, 6-(3,4-dihydroxybenzylamino)purine, 6-(3,5-dihydroxybenzylamino)purine, 6-(3,4-dihydroxybenzylamino)purine, 6-(2,3-ethylenedioxybenzylamino)purine, 6-(2,4-dihydroxybenzylamino)purine, 6-(2,5-dihydroxybenzylamino)purine, 6-(2,6-dihydroxybenzylamino)purine, 6-(3,4-dimethoxybenzylamino)purine, 6-(3,5-dimethoxybenzylamino)purine, 6-(2,3-dimethoxybenzylamino)purine, 6-(2,4-dimethoxybenzylamino)purine, 6-(2,5-dimethoxybenzylamino)purine, 6-(2,6-dimethoxybenzylamino)purine, 6-(3-hydroxy-4-methoxybenzylamino)purine, 6-(2-hydroxy-3-methoxybenzylamino)purine, 6-(4-hydroxy-3-methoxybenzylamino)purine, 6-(2-hydroxy-4-methoxybenzylamino)purine, 6-(4-hydroxy-2-methoxybenzylamino)purine, 6-(2-hydroxy-5-methoxybenzylamino)purine, 6-(3-hydroxy-4-methoxybenzylamino)purine, 6-(4-hydroxy-3-methoxybenzylamino)purine, 6-(2-hydroxy-6-methoxybenzylamino)purine, 6-(3-hydroxy-5-methoxybenzylamino)purine, 6-(4,5-dimethoxy-2-nitrobenzylamino)purine, 6-(3,4-dimethylbenzylamino)purine, 6-(2,3-dimethylbenzylamino)purine, 6-(2,4-dimethylbenzylamino)purine, 6-(2,6-dimethylbenzylamino)purine, 6-(2,6-dimethyl-4-hydroxybenzylamino)purine, 6-(3,5-dimethyl-4-hydroxybenzylamino)purine, 6-(2-fluoro-4-hydroxybenzylamino)purine, 6-(3-fluoro-4-methylbenzylamino)purine, 6-(3,4-dinitrobenzylamino)purine, 6-(3,5-dinitrobenzylamino)purine, 6-(2-methyl-5-nitrobenzylamino)purine, 6-(3-methyl-4-nitrobenzylamino)purine, 6-(3,4-diiodo-4-hydroxybenzylamino)purine, 6-(2-chloro-3,4-dimethoxybenzylamino)purine, 6-(4-chloro-3,5-dinitrobenzylamino)purine, 6-(2-chloro-4-fluorobenzylamino)purine, 6-(3-chloro-4-fluorobenzylamino)purine, 6-(2-chloro-6-methylbenzylamino)purine, 6-(3-chloro-2-methylbenzylamino)purine, 6-(3-chloro-4-methylbenzylamino)purine, 6-(5-chloro-2-methoxybenzylamino)purine, 6-(2-chloro-4-fluorobenzylamino)purine, 6-(4-chloromethylbenzylamino)purine, 6-(2-chloro-5-nitrobenzylamino)purine, 6-(2-chloro-6-nitrobenzylamino)purine, 6-(4-chloro-3-nitrobenzylamino)purine, 6-(5-chloro-2-nitrobenzylamino)purine, 6-(3-bromo-4-hydroxybenzylamino)purine, 6-(3,5-dibromo-4-hydroxybenzylamino)purine, 6-(3-bromo-4-methoxybenzylamino)purine, 6-(4-bromomethylbenzylamino)purine, 6-(4-butoxybenzylamino)purine, 6-(4-butoxybenzylamino)purine, 6-(4-/t-butyl/benzylamino)purine, 6-(4-t-butyl-2,6-dimethylbenzylamino)purine, 6-(2-aminobenzylamino)purine, 6-(3-aminobenzylamino)purine, 6-(4-aminobenzylamino)purine, 6-(2-amino-6-chlorobenzylamino)purine, 6-(3-amino-4-chlorobenzylamino)purine, 6-(2-amino-3-chlorobenzylamino)purine, 6-(2-amino-4-chlorobenzylamino)purine, 6-(2-amino-6-chlorobenzylamino)purine, 6-(2,6-diamino-3-chlorobenzylamino)purine, 6-(2,6-diamino-4-chlorobenzylamino)purine, 6-(4-amino-3-chlorobenzylamino)purine, 6-(4-amino-5-dichlorobenzylamino)purine, 6-(5-amino-2-methylbenzylamino)purine, 6-(2-amino-3-nitrobenzylamino)purine, 6-(4-amino-3-nitrobenzylamino)purine, 6-(4-benzyloxybenzylamino)purine, 6-(3-acetylbenzylamino)purine, 6-(2-acetylbenzylamino)purine, 6-(2,3,4-trimethoxybenzylamino)purine, 6-(2,4,5-trimethoxybenzylamino)purine, 6-(2,4,6-trimethoxybenzylamino)purine, 6-(3,4,5-trimethoxybenzylamino)purine, 6-(2,4,6-trimethoxybenzylamino)purine, 6-(2,3,4-trihydroxybenzylamino)purine, 6-(2,4,6-trihydroxybenzylamino)purine, 6-(2,3,4-trihydroxybenzylamino)purine, 6-(3,4,5-trihydroxybenzylamino)purine, 6-(2,4,6-trihydroxybenzylamino)purine, 6-(2,4,5-trichlorobenzylamino)purine, 6-(2,4,5-trichlorobenzylamino)purine, 6-(2,4,6-trichlorobenzylamino)purine, 6-(2,3,4-trichlorobenzylamino)purine, 6-(2,3,5-trichlorobenzylamino)purine, 6-(2,3,6-trichlorobenzylamino)purine, 6-(2,5,6-trichlorobenzylamino)purine, 6-anilinopurine, 6-(2,4-bis(trifluoromethyl)anilino)purine, 6-(2,5-bis(trifluoromethyl)anilino)purine, 6-(2,4-bis(trifluoromethyl)anilino)purine, 6-(3,5-bis(trifluoromethyl)anilino)purine, 6-(2-bromoanilino)purine, 6-(3-bromoanilino)purine, 6-(4-bromoanilino)purine, 6-(4-bromo-2-chloroanilino)purine, 6-(4-bromo-3-chloroanilino)purine, 6-(2-bromo-6-chloro-4-(trifluoromethyl)anilino)purine, 6-(4-bromo-5,6-difluoroanilino)purine, 6-(2-bromo-4,6-difluoroanilino)purine, 6-(4-bromo-2,6-difluoroanilino)purine, 6-(4-bromo-2-fluoroanilino)purine, 6-(2-bromo-4-fluoroanilino)purine, 6-(2-bromo-4-methylanilino)purine, 6-(3-bromo-2-methylanilino)purine, 6-(4-bromo-3-methylanilino)purine, 6-(2-bromo-4-(trifluoromethoxy)anilino)purine, 6-(3-bromo-4-(trifluoromethoxy)anilino)purine, 6-(4-bromo-2-(trifluoromethoxy)anilino)purine, 6-(2-bromo-4,5,6-trifluoroanilino)purine, 6-(2,4-dibromoanilino)purine, 6-(2,5-dibromoanilino)purine, 6-(2,4-dibromo-3,6-dichloroanilino)purine, 6-(2,6-dibromo-4-fluoroanilino)purine, 6-(2,6-dibromo-4-(trifluoromethoxy)anilino)purine, 6-(2,4-dibromo-6-(trifluoromethyl)anilino)purine, 6-(2,6-dibromo-4-(trifluoromethyl)anilino)purine, 6-(2,3-dichloroanilino)purine, 6-(2,4-dichloroanilino)purine, 6-(2,5-dichloroanilino)purine, 6-(2,6-dichlorooanilino)purine, 6-(3,4-dichloroanilino)purine, 6-(3,5-dichloroanilino)purine, 6-(2,6-dichloro-4-(trifluoromethoxy)anilino)purine, 6-(2,4-dichloro-6-(trifluoromethyl)anilino)purine, 6-(2,6-dichloro-4-(trifluoromethyl)anilino)purine, 6-(2,3-difluoroanilino)purine, 6-(2,4-difluoroanilino)purine, 6-(2,5-difluoroanilino)purine, 6-(2,6-difluoroanilino)purine, 6-(3,4-difluoroanilino)purine, 6-(3,5-difluoroanilino)purine, 6-(2-difluoromethoxyanilino)purine, 6-(2-difluoromethoxy-5-nitroanilino)purine, 6-(2,3-difluoro-6-nitroanilino)purine, 6-(2,4-difluoro-6-nitroanilino)purine, 6-(2,4-difloroanilino)purine, 6-(2,3-dimethylanilino)purine, 6-(2,4-dimethylanilino)purine, 6-(2,3-dimethyl-6-nitroanilino)purine, 6-(2,4-dimethoxyanilino)purine, 6-(2,3-dimethoxyanilino)purine, 6-(2,3-dinitro-6-methylanilino)purine, 6-(4-hydroxy-2-methylanilino)purine, 6-(2-chloroanilino)purine, 6-(3-chloroanilino)purine, 6-(4-chloroanilino)purine, (3-chloro-2,6-dibromo-4-fluoroanilino)purine, 6-(2-chloro-4-fluoroanilino)purine, 6-(2-chloro-5-fluoroanilino)purine, 6-(2-chloro-6-fluoroanilino)purine, 6-(3-chloro-2-fluoroanilino)purine, 6-(3-chloro-4-fluoroanilino)purine, 6-(4-chloro-2-fluoroanilino)purine, 6-(5-chloro-2-fluoroanilino)purine, 6-(2-chloro-4-fluoro-5-methylanilino)purine, 6-(5-chloro-4-fluoro-2-nitroanilino)purine, 6-(5-chloro-2-hydroxyanilino)purine, 6-(4-chloro-2-iodoanilino)purine, 6-(2-chloro-4-iodoanilino)purine, 6-(2-chloro-6-methylanilino)purine, 6-(3-chloro-2-methylanilino)purine, 6-(3-chloro-4-(trifluoromethoxy)anilino)purine, 6-(4-chloro-2-(trifluoromethoxy)anilino)purine, 6-(2-fluoroanilino)purine, 6-(3-fluoroanilino)purine, 6-(4-fluoroanilino)purine, 6-(2-fluoro-4-iodoanilino)purine, 6-(2-fluoro-5-nitroanilino)purine 6-(2-fluoro-4-methylanilino)purine, 6-(3-fluoro-2-methylanilino)purine, 6-(3-fluoro-4-methylanilino)purine, 6-(4-fluoro-2-methylanilino)purine, 6-(3-fluoro-4-methylanilino)purine, 6-(5-fluoro-2-methylanilino)purine, 6-(4-fluoro-2-nitroanilino)purine, 6-(4-fluoro-3-nitroanilino)purine, 6-(2-jodoanilino)purine, 6-(2-fluoro-4-(trifluoromethyl)anilino)purine, 6-(4-iodo-2-methylanilino)purine, 6-(2-methoxyanilino)purine, 6-(3-methoxyanilino)purine, 6-(4-methoxyanilino)purine, 6-(2-methoxy-5-methylanilino)purine, 6-(2-methoxy-6-methylanilino)purine, 6-(4-methoxy-2-methylanilino)purine, 6-(5-methoxy-2-methylanilino)purin, 6-(4-methoxy-3-(trifluoromethyl)anilino)purin, 6-(2-methylanilino)purine, 6-(4-methylanilino)purine, 6-(3-methylanilino)purine, 6-(2-methyl-3-(trifluoromethoxy)anilino)purine, 6-(2-methyl-4-(trifluoromethoxy)anilino)purine, 6-(2-(methylthio)anilino)purine, 6-(4-(methylthio)anilino)purine, 6-(2-nitroanilino)purine, 6-(3-nitroanilino)purine, 6-(4-nitroanilino)purine, 6-(2-nitro-4,5,6-trifluoroanilino)purine, 6-(2-nitro-4-(trifluoromethoxy)anilino)purine, 6-(2-nitrotetrafluoroanilino)purine, 6-(2,3,4,5,6-pentabromoanilino)purine, 6-(2,3,4,5,6-pentafluoroanilino)purine, 6-(2,3,4,5-tetrachloroanilino)purine, 6-(2,3,5,6-tetrachloroanilino)purine, 6-(4-(1,1,2,2-tetrafluoroethoxy)anilino)purine, 6-(2,3,4,5,-tetrafluoroanilino)purine, 6-(2,3,4,6,-tetrafluoroanilino)purine, 6-(2,3,5,6,-tetrafluoroanilino)purine, 6-(2,3,5,6-tetrafluoro-4-(trifluoromethyl)anilino)purine, 6-(2,4,6-tribromoanilino)purine, 6-(2,4,6-tribromo-3,5-dijodoanilino)purine, 6-(2,3,4-trichloroanilino)purine, 6-(2,4,5-trichloroanilino)purine, 6-(2,4,6-trichloroanilino)purine, 6-(2,4,5-trifluoroanilino)purine, 6-(2,3,5-trifluoroanilino)purine, 6-(2,3,6-trifluoroanilino)purine, 6-(2,3,4-trifluoroanilino)purine, 6-(2-trifluoromethoxyanilino)purine, 6-(3-trifluoromethoxyanilino)purine, 6-(4-trifluoromethoxyanilino) purine, 6-(2,3,4-trifluoro-6-nitroanilino)purine, 6-(2,4,5-trimethylanilino)purine, 6-(2,4,6-trimethylanilino)purine, 6-(3-chloro-5-aminoanilino)purine, 6-(3-chloro-4-carboxyanilino)purine, 6-(3-amino-4-chloroanilino)purine, 6-(3-chloro-4-aminoanilino)purine, 6-(3-carboxy-4-hydroxyanilino)purine.

The starting material for the preparation of the compounds of the general formula I is 6-chloropurine, synthesised from hypoxantin using $POCl_3$ according to the literature (Davoll and Blowy, J. Am. Chem. Soc. 73:2936 (1957)) or commercially available (Sigma, Aldrich, Fluka).

Another starting material for the preparation of the compounds of the general formula I is 6-bromopurine, synthesised from hypoxantin using n-pentyl nitrite in tribromomethane, or commercially available.

According to the present invention the new heterocyclic derivatives based on $N^6$-substituted adenine having formula I, wherein R2 and R6 are as described herein before, may be prepared from heterocyclic derivative having formula I, wherein R6 represents bromine, chlorine or methylmercapto group and R2 is as described herein before, by a nucleophilic substitution in order to convert chlorine, bromine, or methylmercapto group at R6 position to any other meaning of substituent R6, as described herein before, to obtain the compound having formula I.

A further method according to the present invention is the preparation of the compounds of formula I, characterised in that the heterocyclic derivative having formula I, wherein R2 is hydrogen and R6 represents an amino group, is substituted at the R6 position by the reaction with an aldehyde having the formula R6'-CHO, wherein R6' is described herein before, in order to convert the amino group at the R6 position to any other meaning of substituent R6, as described herein before, to obtain the compound of formula I.

This invention also concerns heterocyclic compounds based on $N^6$-substituted adenine according formula I for use as pharmaceuticals.

This invention further concerns heterocyclic compounds based on $N^6$-substituted adenine according to claim 1 of formula I for use as growth regulators of plant, mammal, microorganisms, yeast and fungal cells.

This invention also concerns heterocyclic compounds based on $N^6$-substituted adenine according to claim 1 of formula I for use as cosmetics.

Object of the present invention are also pharmaceuticals, cosmetics or growth regulators, which contain compound of the formula I or their pharmaceutically acceptable salt, including a pharmaceutical carrier.

A further object of this invention is the use of heterocyclic compounds based on $N^6$-substituted adenine according to claim 1 of formula I, for preparation of affinity absorption matrices, immobilised enzymes for process control, immunoassay reagents, diagnostic samples, as well as compounds and oligonucleotides, labeled by $^{14}C$, $^3H$, avidin or biotin.

This invention also concerns method of using a compound of formula I or their pharmaceutically acceptable salt, including a pharmaceutical carrier for preparation of a pharmaceutical composition destined for use as mitotic or antimitotic compound, especially for treating cancer, psoriasis, rheumatoid arthritis, lupus, type I diabetes, multiple sclerosis, restenosis, polycystic kidney disease, graft rejection, graft versus host disease and gout, parasitoses such as those caused by fungi or protists, or Alzheimer's disease, or as antineurogenerative drugs, or to suppress immunostimulation or for the treatment of proliferative skin diseases.

Object of the invention is further the use of heterocyclic compounds based on $N^6$-substituted adenine according to claim 1 of formula I for use as growth regulators in agriculture, especially for increasing of yield and quality of agricultural products.

This invention also concerns heterocyclic compounds based on $N^6$-substituted adenine of formula I for use as cosmetics for inhibiting ageing and senescence of mammalian epidermal cells, such as keratinocytes or fibroblasts.

A further object of this invention is the use of heterocyclic compounds based on $N^6$-substituted adenine of formula I as growth regulator in tissue cultures for stimulation of proliferation and morphogenesis.

This invention also concerns heterocyclic compounds based on $N^6$-substituted adenine of formula I, for the preparation of a composition and its using for plant and mammalian embryonic cells and embryos (esp. oocytes) cloning.

This invention also concerns heterocyclic compounds based on $N^6$-substituted adenine according to claim 1 having formula I, for preparation of a composition and its using for suppressing immunostimulation e.g. arthritis or in suppression of transplant rejection in mammals.

Therapeutic Administration

Suitable routes for administration include oral, rectal, topical (including dermal, ocular, buccal and sublingual), vaginal and parenteral (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

The therapeutic composition comprise about 1% to about 95% of the active ingredient, single-dose forms of administration preferably comprising about 20% to about 90% of the active ingredient and administration forms which are not single-dose preferably comprising about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical compositions of the present invention are prepared in a manner known per se, for example by means of conventional mixing, granulating, coating, dissolving or lyophilising processes.

Preferably, solutions of the active ingredient, and in addition also suspensions or dispersions, especially isotonic aqueous solutions, dispersions or suspensions, are used, it being possible for these to be prepared before use, for example in the case of lyophilised compositions which comprise the active substance by itself or together with a carrier, for example mannitol. The pharmaceutical compositions can be sterilised and/or comprise excipients, for example preservatives, stabilisers, wetting agents and/or emulsifiers, solubilizing agents, salts for regulating the osmotic pressure and/or buffers, and they are prepared in a manner known per se, for example by means of conventional dissolving or lyophilising processes. The solutions or suspensions mentioned can comprise viscosity-increasing substances, such as sodium carboxymethylcellulose, dextran, polyvinylpyrrolidone or gelatine.

Suspensions in oil comprise, as the oily component, the vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, acid, arachidonic acid, behenic acid or corresponding unsaturated acids, for example oleic acid, elaidic acid, euric acid, brasidic acid or linoleic acid, if appropriate with the addition of antioxidants, for example vitamin E, β-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and made up of glycerides and polyethylene glycol esters; from Gattefoseé, Paris), "Labrasol" (saturated polyglycolated glycerides prepared by an alcoholysis of TCM and made up of glycerides and polyethylene glycol esters; from Gattefoseé, Paris) and/or "Miglyol 812" (triglyceride of saturated fatty acids of chain length $C_8$ to $C_{12}$ from Hüls AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example in ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients.

Suitable carriers are, in particular, fillers, such as sugars, for example lactose, sucrose, mannitol or sorbitol, cellulose preparations and/or calcium phosphates, for example tricalcium diphosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidine, and/or, if desired, desintegrators, such as the above mentioned starches, and furthermore carboxymethyl-starch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or characterisation of different doses of active ingredient.

Pharmaceutical compositions, which can be used orally, are also hard capsules of gelatine and soft, closed capsules of gelatine and a plasticiser, such as glycerol or sorbitol. The hard capsules can contain the active ingredient in the form of granules, mixed for example with fillers, such as maize starch, binders and/or lubricants, such as talc or magnesium stearate, and stabilisers if appropriate. In soft capsules, the active ingredient is preferably dissolved or suspended in suitable liquid excipients, such as greasy oils, paraffin oil or liquid polyethylene glycol or fatty acid esters of ethylene glycol or propylene glycol, it being likewise possible to add stabilisers and detergents, for example of the polyethylene sorbitan fatty acid ester type.

Other oral forms of administration are, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parental administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate stabilisers. The active ingredient can also be present here in the form of a lyophilisate, if appropriate together with excipients, and be dissolved before parenteral administration by addition of suitable solvents. Solutions such as are used, for example, for parental administration can also be used as infusion solutions. Preferred preservatives are, for example antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists, in particular, hydrocarbons, for example vaseline, paraffin oil or hard paraffins, which preferably comprise suitable hydroxy compounds, such as fatty alcohols or esters thereof, for example cetyl alcohol or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, the fatty alcohols. They also contain emulsifiers and/or additives mentioned in connection with the ointments which increase uptake of water.

Creams are oil-in-water emulsions, which comprise more than 50% of water. Oily bases used are, in particular, fatty alcohols, for example lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding non-ionic emulsifiers, for example fatty acid esters of polyalcohols or ethyleneoxy adducts thereof, such as polyglyceric acid fatty acid esters or polyethylene sorbitan fatty esters (Tweens), and furthermore polyoxyethylene fatty alcohol ethers or polyoxyethylene fatty acid esters, or corresponding ionic emulsifiers, such as alkali metal salts of fatty alcohol sulphates, for example sodium lauryl sulphate, sodium cetyl sulphate or sodium stearyl sulphate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and/or polyethylene glycols, and furthermore preservatives and odoriferous substances.

Pastes are creams and ointments having secretion-absorbing powder constituents, such as metal oxides, for example titanium oxide or zinc oxide, and furthermore talc and/or aluminium silicates, which have the task of binding the moisture or secretions present.

Foams are administered from pressurised containers and they are liquid oil-in-water emulsions present in aerosol foam. As the propellant gases halogenated hydrocarbons, such as polyhalogenated alkanes, for example dichlorofluoromethane and dichlorotetrafluoroethane, or, preferably, non-halogenated gaseous hydrocarbons air, $N_2O$, or carbon dioxide are used. The oily phases used are, inter alia, those mentioned above for ointments and creams, and the additives mentioned there are likewise used.

Tinctures and solutions usually comprise an aqueous-ethanolic base to which, humectants for reducing evaporation, such as polyalcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with ethanol, and, if necessary, other excipients and additives, are admixed.

The present invention further provides veterinary compositions comprising at least one active ingredient as above defined together with a veterinary carrier therefor. Veterinary carriers are materials for administering the composition and may be solid, liquid or gaseous materials, which are inert or acceptable in the veterinary art and are compatible with the active ingredient. These veterinary compositions may be administered orally, parenterally or by any other desired route.

The invention also relates to a process or method for treatment of the disease states mentioned above. The compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of a compound of the present invention is administered here for a body weight of about 70 kg.

FIGURES

In FIG. 1 there is shown the inhibition of growth of K562 (A) and CEM (B) tumour cell lines by tested compounds. Cytotoxicity was determined in the presence of Calcein AM. Activity is presented as percentage of maximal activity (in the absence of inhibitors). iP: isopentenyladenine; 2F BAP: 6-(2-fluorobenzylamino)purine; 2Cl BAP: 6-(2-chlorobenzylamino)purine; 2OH-3OCH$_3$ BAP: 6-(2-hydroxy-3-methoxybenzylamino)purine.

In FIG. 2 there are shown senescent cells in culture of human fibroblasts (B) (the other cells (A)) stained blue due to the action of β-galactosidase on the substrate X-gal (5-bromo-4-chloro-3-indolyl-β-D-galactopyranosid) (1 mg/ml).

In FIG. 3 there is shown the induced apoptosis in tumour cells MCF-7 cell line after application of cytokinin 6-(2-hydroxy-3-methoxybenzylamino)purine. A MCF-7, apoptotic cells: 6 h, 12, 20 µM, B MCF-7, secondary necrotic cells (i.e. necrosis following apoptosis), 12 h, 12, 40 µM; C MCF-7, necrotic cells, 24 h, 12, 40 µM. Anexin FITC V (Mol. Probes) and propidiun iodide staining: anexin—green, PI—red.

FIG. 4 shows the apoptotic cells detection using Anexin (green fluorescence) and Hoechstem 33285 (blue fluorescence) staining. Analysed using "Olympus image analysis" after treatment of MCF-7 tumour cells by 6-(2-hydroxy-3-methoxybenzylamino)purine. A,B—control cells without treatment; C,D—apoptotic cells (condensation of chromatin); A,C—fluorescence microscopy; BD—fluorescence image analysis.

FIG. 5 shows the effect of tested compounds on retention of chlorophyll in excised wheat leaf tips. Values are expressed as % of initial chlorophyll content of fresh leaves before the incubation. Error bars show standard deviations of the mean for 5 replicate determinations. Dashed line indicates control incubation without any cytokinin, which was 31,7±0,9.

In FIG. 6 there is shown the effect of tested compounds on fresh weight yield of tobacco callus culture. Error bars show standard deviations of the mean for 5 replicate determinations. Dashed line indicates the value for the control treatment without any cytokinin, 2,2±0,4 g.

FIG. 7 shows the effect of tested compounds on dark induction of betacyanin synthesis in *Amaranthus caudatus* cotyledon/hypocotyl explants. Error bars show standard deviations of the mean for 5 replicate determinations. Dashed line indicates the values for the control treatment without added cytokinin, 0,043±0.009. Values represent the difference in O.D. units between absorption at 537 and 620 nm.

FIG. 8 shows the relative number of explants with at least one brown leaf in function of culture time (: BA, ●: mT, : mMeOBAP).

In FIG. 9 there is shown the relative number of dead explants in relation to culture time (: BA, ●: mT, : mMeOBAP).

In FIG. 10 there is shown at left: dead *Rosa hybrida* explant on BA containing medium; at right: vigorous *Rosa hybrida* plantlet after 121 days of cultivation on mMeOBAP containing medium.

The following examples serve to illustrate the invention without limiting the scope thereof.

EXAMPLES

Example 1

6-(3-chlorobenzylamino)purine 3 mmol of 6-chloropurine were dissolved in 15 ml of butanol. Subsequently, 4 mmol of 3-chlorobenzylamine and 5 mmol triethylamine were added and the mixture was heated at 90° C. for 4 hours. After cooling, the precipitated product was filtered off, washed with cold water and n-butanol and crystallised from ethanol or dimethylformamide. M.p.=252° C., TLC ($CHCl_3$:MeOH:conc. $NH_4OH$ (8:2:0.2, v/v/v)): single spot; HPLC: purity>98%. Yield 95%.

TABLE 1

Compounds Prepared by the Method of Example 1

| R6 Substituent | CHN analyses calculated/found | | | ESI-MS [M + H$^+$] |
|---|---|---|---|---|
| | % C | % H | % N | |
| 2-fluorobenzylamino | 59.3/59.05 | 4.1/3.8 | 28.8/27.8 | 244 |
| 3-fluorobenzylamino | 59.3/59.1 | 4.1/3.9 | 28.8/27.7 | 244 |
| 4-fluorobenzylamino | 59.3/59.2 | 4.1/3.9 | 28.8/27.9 | 244 |
| 2-chlorobenzylamino | 55.5/55.7 | 3.8/4.2 | 27.0/26.0 | 260 |
| 3-chlorobenzylamino | 55.5/55.2 | 3.8/3.9 | 27.0/26.2 | 260 |
| 4-chlorobenzylamino | 55.5/55.3 | 3.8/3.8 | 27.0/26.6 | 260 |
| 2-bromobenzylamino | 47.4/47.6 | 3.3/3.5 | 23.0/22.5 | 304 |
| 2-bromobenzylamino | 47.4/47.1 | 3.3/3.4 | 23.0/23.1 | 304 |
| 2-bromobenzylamino | 47.4/47.8 | 3.3/3.4 | 23.0/22.3 | 304 |
| 3-jodobenzylamino | 41.0/41.4 | 2.8/2.8 | 20.0/19.5 | 352 |
| 2-methylbenzylamino | 65.2/64.9 | 5.5/5.8 | 29.3/29.8 | 240 |
| 3-methylbenzylamino | 65.2/64.7 | 5.5/6.0 | 29.3/29.9 | 240 |
| 4-methylbenzylamino | 65.2/65.7 | 5.5/5.4 | 29.3/27.5 | 240 |
| 2-methoxylbenzylamino | 61.2/61.0 | 5.1/5.5 | 27.4/26.6 | 256 |
| 3-methoxylbenzylamino | 61.2/61.0 | 5.1/5.3 | 27.4/27.5 | 256 |
| 4-methoxylbenzylamino | 61.2/60.7 | 5.1/5.3 | 27.4/26.7 | 256 |
| 3-nitrobenzylamino | 53.3/53.1 | 3.7/3.6 | 31.1/30.8 | 271 |
| 4-nitrobenzylamino | 53.3/53.0 | 3.7/3.5 | 31.1/30.8 | 271 |
| 2,4-dichlorobenzylamino | 49.0/49.4 | 3.1/3.1 | 23.8/23.1 | 295 |
| 3,4-dichlorobenzylamino | 49.0/49.1 | 3.1/3.2 | 23.8/23.0 | 295 |
| 2,3-dihydroxybenzylamino | 56.2/55.7 | 3.5/3.2 | 27.2/27.9 | 258 |
| 2,4-dihydroxybenzylamino | 56.2/55.4 | 3.5/3.4 | 27.2/27.7 | 258 |
| 3,4-dihydroxybenzylamino | 56.2/55.5 | 3.5/3.4 | 27.2/27.7 | 258 |
| 2-hydroxy-3-methoxybenzylamino | 57.5/57.2 | 4.8/4.6 | 25.8/26.4 | 272 |
| 2-hydroxy-4-methoxybenzylamino | 57.5/57.1 | 4.8/4.5 | 25.8/26.6 | 272 |
| 4-hydroxy-3-methoxybenzylamino | 57.5/57.3 | 4.8/4.7 | 25.8/26.2 | 272 |
| 3-hydroxy-4-methoxybenzylamino | 57.5/57.0 | 4.8/4.5 | 25.8/26.7 | 272 |
| 2,3-dimethoxybenzylamino | 58.9/59.3 | 5.3/5.48 | 24.5/24.5 | 286 |
| 2,4-dimethoxybenzylamino | 58.9/59.3 | 5.3/4.9 | 24.5/25.5 | 286 |
| 3,4-dimethoxybenzylamino | 58.9/59.7 | 5.3/5.6 | 24.5/24.8 | 286 |
| 3,5-methoxybenzylamino | 58.9/59.7 | 5.3/5.32 | 24.5/24.4 | 286 |
| 2,4,6-trimethoxybenzylamino | 57.1/57.3 | 5.4/5.3 | 22.2/22.8 | 316 |
| 3,4,5-trimethoxybenzylamino | 57.1/57.1 | 5.4/5.2 | 22.2/22.5 | 316 |
| 2,4-difluorobenzylamino | 55.2/54.5 | 3.5/3.1 | 26.8/27.2 | 262 |
| 3,5-difluorobenzylamino | 55.2/54.8 | 3.5/3.3 | 26.8/27.3 | 262 |
| 2,3,4-trifluorobenzylamino | 51.6/51.1 | 2.9/2.7 | 25.1/25.5 | 280 |
| 3-chloro-4-fluorobenzylamino | 51.9/50.9 | 3.3/3.4 | 25.2/25.7 | 278 |
| 2-(trifluoromethyl)benzylamino | 53.2/52.9 | 3.4/3.1 | 23.9/24.5 | 294 |
| 3-(trifluoromethyl)benzylamino | 53.2/52.9 | 3.4/3.2 | 23.9/24.6 | 294 |
| 4-(trifluoromethyl)benzylamino | 53.2/52.7 | 3.4/3.1 | 23.9/24.8 | 294 |
| Anilino | 62.5/62.2 | 3.3/3.1 | 33.1/33.8 | 212 |
| 2-fluoroanilino | 57.6/57.0 | 3.5/3.4 | 30.6/31.1 | 230 |
| 3-fluoroanilino | 57.6/57.1 | 3.5/3.3 | 30.6/31.5 | 230 |
| 4-fluoroanilino | 57.6/57.0 | 3.5/3.3 | 30.6/31.5 | 230 |
| 2-chloroanilino | 53.8/53.2 | 3.3/3.2 | 28.5/29.3 | 246 |
| 3-chloroanilino | 53.8/53.1 | 3.3/3.3 | 28.5/28.9 | 246 |
| 4-chloroanilino | 53.8/53.4 | 3.3/3.2 | 28.5/29.3 | 246 |
| 2-bromoanilino | 45.5/45.0 | 2.8/2.7 | 24.1/24.7 | 291 |
| 3-bromoanilino | 45.5/25.0 | 2.8/2.7 | 24.1/24.9 | 291 |
| 4-bromoanilino | 45.5/44.7 | 2.8/2.4 | 24.1/25.1 | 291 |
| 2-jodoanilino | 39.2/38.5 | 2.4/2.1 | 20.8/21.3 | 338 |
| 2-methoxyanilino | 59.7/59.4 | 4.6/4.6 | 29.0/29.4 | 242 |
| 3-methoxyanilino | 59.7/59.1 | 4.6/4.5 | 29.0/29.7 | 242 |
| 4-methoxyanilino | 59.7/59.2 | 4.6/4.5 | 29.0/29.6 | 242 |
| 2-methylanilino | 64.0/63.7 | 4.9/4.7 | 31.1/31.8 | 226 |
| 3-methylanilino | 64.0/63.7 | 4.9/4.8 | 31.1/31.9 | 226 |
| 4-methylanilino | 64.0/63.5 | 4.9/4.7 | 31.1/32.0 | 226 |

Example 2

Mixture of 10 mmol adenine, 12 mmol 2-methoxybenzaldehyde a 5 ml 98-100% formic acid was refluxed for 3 days. After formic acid evaporation, the resulting material was cooled and subsequently washed with 40 ml of diethylether. Solid residue was boiled with 60 ml of water, filtered of and crude product crystallised from ethanol. Yield 45%.

TABLE 2

Compounds Prepared by the Method of Example 2

| R6 Substituent | % C | % H | % N | ESI-MS [M + H$^+$] |
|---|---|---|---|---|
| | \multicolumn{3}{c}{CHN analyses calculated/found} | |
| 2-chlorobenzylamino | 55.5/54.7 | 3.8/4.1 | 27.0/27.6 | 260 |
| 3-chlorobenzylamino | 55.5/54.8 | 3.8/3.9 | 27.0/27.2 | 260 |
| 4-chlorobenzylamino | 55.5/54.5 | 3.8/4.0 | 27.0/27.6 | 260 |
| 2-bromobenzylamino | 47.4/46.7 | 3.3/3.5 | 23.0/23.4 | 304 |
| 2-bromobenzylamino | 47.4/46.5 | 3.3/3.4 | 23.0/23.3 | 304 |
| 2-methylbenzylamino | 65.2/64.8 | 5.5/5.9 | 29.3/29.8 | 240 |
| 3-methylbenzylamino | 65.2/64.8 | 5.5/5.7 | 29.3/30.1 | 240 |
| 4-methylbenzylamino | 65.2/64.7 | 5.5/5.8 | 29.3/29.9 | 240 |
| 2-methoxylbenzylamino | 61.2/60.3 | 5.1/5.3 | 27.4/27.9 | 256 |
| 3-methoxylbenzylamino | 61.2/61.00 | 5.1/5.3 | 27.4/27.9 | 256 |
| 4-methoxylbenzylamino | 61.2/60.4 | 5.1/5.2 | 27.4/28.3 | 256 |
| 2,4-dichlorobenzylamino | 49.0/48.4 | 3.1/3.0 | 23.8/24.4 | 295 |
| 3,4-dichlorobenzylamino | 49.0/48.6 | 3.1/3.1 | 23.8/24.4 | 295 |
| 2,3-dimethoxybenzylamino | 58.9/58.8 | 5.3/5.4 | 24.5/24.7 | 286 |
| 2,4-dimethoxybenzylamino | 58.9/58.4 | 5.3/5.8 | 24.5/25.5 | 286 |
| 3,4-dimethoxybenzylamino | 58.9/58.5 | 5.3/5.6 | 24.5/25.2 | 286 |
| 3,5-dimethoxybenzylamino | 58.9/58.7 | 5.3/5.4 | 24.5/25.0 | 286 |
| 2,4,6-trimethoxybenzylamino | 57.1/57.2 | 5.4/5.4 | 22.2/22.5 | 316 |
| 3,4,5-trimethoxybenzylamino | 57.1/57.4 | 5.4/5.5 | 22.2/22.5 | 316 |

Example 3

In vitro Cytotoxic Activity of Novel Compounds

One of the parameters used, as the basis for cytotoxicity assays, is the metabolic activity of viable cells. For example, a microtiter assay, which uses the Calcein AM, is now widely used to quantitate cell proliferation and cytotoxicity. For instance, this assay is used in drug screening programs and in chemosensitivity testing. Because only metabolically active cells cleave Calcein AM, these assays detect viable cells exclusively. The quantity of reduced Calcein AM corresponds to the number of vital cells in the culture.

Human T-lymphoblastic leukemia cell line CEM; promyelocytic HL-60 and monocytic U937 leukemias; breast carcinoma cell lines MCF-7, BT549, MDA-MB-231; glioblastoma U87MG cells; cervical carcinoma cells HELA; sarcoma cells U2OS and Saos2; hepatocellular carcinoma HepG2; mouse fibroblasts NIH3T3; mouse immortalized bone marrow macrophages B2.4 and B10A.4; P388D1 and L1210 leukemia; B16 and B16F10 melanomas were used for routine screening of compounds. The cells were maintained in Nunc/Corning 80 cm$^2$ plastic tissue culture flasks and cultured in cell culture medium DMEM with 5 g/l glucose, 2 mM glutamine, 100 U/ml penicillin, 100 µg/ml streptomycin, 10% fetal calf serum and sodium bicarbonate).

The cell suspensions that were prepared and diluted according to the particular cell type and the expected target cell density (2.500-30.000 cells per well based on cell growth characteristics) were added by pipette (80 µl) into 96/well microtiter plates. Inoculates were allowed a pre-incubation period of 24 hours at 37° C. and 5% CO$_2$ for stabilisation. Four-fold dilutions of the intended test concentration were added at time zero in 20 µl aliquots to the microtiter plate wells. Usually, test compound was evaluated at six 4-fold dilutions. In routine testing, the highest well concentration was 266.7 µM, but it can be the matter of change dependent on the agent. All drug concentrations were examined in duplicates. Incubations of cells with the test compounds lasted for 72 hours at 37° C., in 5% CO$_2$ atmosphere and 100% humidity. At the end of incubation period, the cells were assayed by using the Calcein AM. Ten microliters of the stock solution were pipetted into each well and incubated further for 1 hours. Fluorescence (FD) was measured with the Labsystem FIA Reader Fluoroscan Ascent (UK). The tumour cell survival (GI$_{50}$) was calculated using the following equitation: TCS=(FD$_{drug\ exposed\ well}$/mean FD$_{control\ wells}$)×100%. The GI$_{50}$ value, the drug concentration lethal to 50% of the tumour cells, was calculated from the obtained dose response curves (FIG. 1).

Cytotoxicity of novel compounds was tested on panel of cell lines of different histogenetic and species origin (Table 3). We show here that equal activities were found in all tumour cell lines tested, however, the non-malignant cells, e.g. NIH3T3 fibroblasts and normal human lymphocytes, were resistant to synthetic inhibitors induced cytotoxicity. As demonstrated in Table 3, GI$_{50}$ for NIH3T3 fibroblasts and normal human lymphocytes was always higher than 250 µM. Effective novel derivatives killed tumour cells in concentrations close to 10-50 µM.

TABLE 3

Cytotoxicity of Novel Compounds for Different Cancer Cell Lines

Cell line tested/IC 50 (μmol/L)

| Compound | HOS | K-562 | MCF7 | B16-FO | NIH-3T3 | G-361 | CEM | HELA | HL60 |
|---|---|---|---|---|---|---|---|---|---|
| Kinetin | >166.7 | >166.7 | >166.7 | | | | 155.1 | | |
| | | 164.1 | | | | | | | |
| IP | >166.7 | 146.9 | >166.7 | | | | 92.2 | | >166.7 |
| | | 162.2 | | | | | | | |
| BAP | >166.7 | 138.9 | 166.1 | | | | >166.7 | | >166.7 |
| | | >166.7 | | | | | | | |
| cis Z | >166.7 | >166.7 | >166.7 | | | | >166.7 | | >166.7 |
| | | >166.7 | | | | | | | |
| acetyl Z | >166.7 | >166.7 | >166.7 | | | | >166.7 | | >166.7 |
| | | >166.7 | | | | | | | |
| MT | >166.7 | 128.4 | >166.7 | 90.6 | | >166.7 | 90.1 | | 79.2 |
| | | 140.2 | | | | | | | |
| OT | >166.7 | >166.7 | >166.7 | 150 | | 103.4 | 69.2 | | 78 |
| | | 67 | | | | | | | |
| 2F BAP | >166.7 | 136.1 | >166.7 | 27.7 | | 106.4 | 98 | | |
| | >166.7 | 70.7 | | | | | 99.5 | | 126.5 |
| 2Cl BAP | 84.9 | 101 | 164.1 | 16.9 | >166.7 | 56.6 | 58.4 | | 109.6 |
| | 100.4 | 90.4 | 128.4 | | | | | | |
| 3Cl BAP | >166.7 | >166.7 | >166.7 | | | 148.6 | >166.7 | | >166.7 |
| 3F BAP | >166.7 | 105.2 | 163.2 | | | >166.7 | >166.7 | | >166.7 |
| 4F BAP | >166.7 | >166.7 | >166.7 | | | >166.7 | 66.4 | | 59.2 |
| 3MeO BAP | >166.7 | >166.7 | >166.7 | 41.5 | >166.7 | 124.7 | >166.7 | | >166.7 |
| | | 76.7 | 149.5 | | | | | | |
| 4MeO BAP | >166.7 | >166.7 | >166.7 | 84.7 | >166.7 | 166.7 | >166.7 | | >166.7 |
| | >166.7 | 118 | >166.7 | | | | | | |
| 2M BAP | >166.7 | 156.6 | >166.7 | | | >166.7 | >166.7 | | >166.7 |
| 3I BAP | >166.7 | 94.7 | 129.9 | | | >166.7 | 124.6 | | 133.3 |
| 4M BAP | >166.7 | 72.8 | 82.8 | | | 160.4 | 72.1 | | 88 |
| 4Cl BAP | >166.7 | >166.7 | >166.7 | | | | >166.7 | | >166.7 |
| 2MeO BAP | >166.7 | 115.8 | 153 | | | | 63.4 | | >166.7 |
| | | | | | | | 98.2 | | |
| 3,5diMeO BAP | | >166.7 | >166.7 | | | | >166.7 | | >166.7 |
| 2,4,6triMeO BAP | | >166.7 | >166.7 | >166.7 | | | 63.6 | | 153.4 |
| | | | | | | | 105.3 | | |
| 4OH3MeO BAP | | >166.7 | >166.7 | >166.7 | | | >166.7 | | >166.7 |
| 3NO$_2$ BAP | | >166.7 | >166.7 | | | | >166.7 | | >166.7 |
| 4NO$_2$ BAP | | >166.7 | >166.7 | >166.7 | | | >166.7 | | >166.7 |
| 2OH3MeO BAP | | >166.7 | 26.6 | 69 | | | 41.6 | | 64.3 |
| | | | | | | | 51 | | 67.8 |
| 3OH4MeO BAP | | >166.7 | >166.7 | >166.7 | | | >166.7 | | >166.7 |
| 3,4diOH BAP | | >166.7 | >166.7 | >166.7 | | | >166.7 | | >166.7 |
| 2F BAP | >166.7 | 136.1 | 108.7 | 130.6 | | 106.4 | 135.7 | | >166.7 |
| | | 70.7 | 128.5 | >166.7 | | | 98.9 | | |
| 3Me BAP | | >166.7 | 102.5 | 164.1 | | | >166.7 | | >166.7 |
| 3Cl4F BAP | | >166.7 | >166.7 | >166.7 | | | 135 | | >166.7 |
| | | >166.7 | >166.7 | | | | 95.8 | | >166.7 |
| 2,3,4triF BAP | | >166.7 | >166.7 | | | | 32 | | >166.7 |
| | | >166.7 | >166.7 | | | | 67 | | >166.7 |
| 2,4diFBAP | | >166.7 | >166.7 | | | | 139.7 | | >166.7 |
| | | >166.7 | >166.7 | | | | 145.8 | | >166.7 |
| Zeatin | | >166.7 | >166.7 | | | | >166.7 | | >166.7 |
| | | >166.7 | >166.7 | | | | >166.7 | | >166.7 |
| Adenine | | >166.7 | >166.7 | | | | >166.7 | | >166.7 |
| | | >166.7 | >166.7 | | | | >166.7 | | >166.7 |

Example 4

Novel Compounds Induce Apoptosis in Tumour Cells

To analyse the mechanisms of induced cytotoxicity by the novel compounds, it is important to distinguish apoptosis from the other major form of cell death, necrosis. First, at the tissue level, apoptosis produces little or no inflammation, since the neighbouring cells, especially macrophages, rather than being released into the extracellular fluid, engulf shrunken portions of the cell. In contrast, in necrosis, cellular contents are released into the extracellular fluid, and thus have an irritant affect on the nearby cells, causing inflammation. Second, at the cellular level, apoptotic cells exhibit shrinkage and blebbing of the cytoplasm, preservation of structure of cellular organelles including the mitochondria, condensation and margination of chromatin, fragmentation of nuclei, and formation of apoptotic bodies, thought not all of these are seen in all cell types. Third, at the molecular level, a number of biochemical processes take an important role in induction of apoptosis. However, majority of them is not well understood, and they result in activation of proteases and nucleases, which finally destruct key biological macromolecules—proteins and DNA.

For detection of apoptotic versus necrotic mode of cell death, two independent methods were employed: assessment of morphology by electron microscopy and analysis of DNA fragmentation by flow-cytometry.

HL-60 cell line was cultured in 6-well culture plates with or without 70 μM concentration of novel derivatives at 37° C. and 5% $CO_2$ for 3-24 hours. Following the incubation, cells were pelleted, washed in Hank's buffered salt solution and processed as described below.

Cells were suspended in 2% glutaraldehyde/PBS, fixed overnight at 4° C., pelleted and embedded into 1% agar (Agar Noble, Difco) thereafter. Agar blocks containing fixed cells were epoxyde polymerised, ultrathin sectioned, osmium tetraoxyde postfixed, uranium acetate contrasted and examined under electron microscope.

Initial phase contrast microscopy examinations indicated that treated HL-60 line exhibit typical morphological features of apoptotic cells, and it was later confirmed by electron microscopy (FIGS. 2 and 3). Typical morphological criteria of apoptosis were identified in cells treated with all novel derivatives tested: chromatin condensation, nuclear fragmentation, cytoplasmatic blebbing, and formation of apoptotic bodies.

Example 5

Immunosuppressive Activity

One of the most important parameters of specific cellular immunity is proliferative response of lymphocytes to antigens or polyclonal mitogens. The majority of normal mammalian peripheral lymphocytes comprise resting cells. Antigens or nonspecific polyclonal mitogens have the capacity to activate lymphoid cells and this is accompanied by dramatic changes of intracellular metabolism (mitochondrial activity, protein synthesis, nucleic acids synthesis, formation of blastic cells and cellular proliferation). Compounds with ability to selectively inhibit lymphocyte proliferation are potent immunosuppressants. Variety of in vitro assays was developed to measure proliferative response of lymphocytes. The most commonly used is $^3$H-thymidine incorporation method.

During cell proliferation, DNA has to be replicated before the cell is divided into two daughter cells. This close association between cell doublings and DNA synthesis is very attractive for assessing cell proliferation. If labelled DNA precursors are added to the cell culture, cells that are about to divide incorporate the labelled nucleotide into their DNA. Traditionally, those assays usually involve the use of radiolabelled nucleosides, particularly tritiated thymidine ($[^3H]$-TdR). The amount of $[^3H]$-TDR incorporated into the cellular DNA is quantified by liquid scintillation counting.

Human heparinized peripheral blood was obtained from healthy volunteers by cubital vein punction. The blood was diluted in PBS (1:3) and mononuclear cells were separated by centrifugation in Ficoll-Hypaque density gradient (Pharmacia, 1.077 g/ml) at 2200 rpm for 30 minutes. Following centrifugation, lymphocytes were washed in PBS and resuspended in cell culture medium (RMPI 1640, 2 mM glutamine, 100 U/ml penicillin, 100 μg/ml streptomycin, 10% fetal calf serum and sodium bicarbonate).

The cells were diluted at target density of 1.100.000 cells/ml were added by pipette (180 μl) into 96/well microtiter plates. Four-fold dilutions of the intended test concentration were added at time zero in 20 μl aliquots to the microtiter plate wells. Usually, test compound was evaluated at six 4-fold dilutions. In routine testing, the highest well concentration was 266.7 μM. All drug concentrations were examined in duplicates. All wells with exception of unstimulated controls were activated with 50 μl of concanavalin A (25 μg/ml). Incubations of cells with test compounds lasted for 72 hours at 37° C., in 5% $CO_2$ atmosphere and 100% humidity. At the end of incubation period, the cells were assayed by using the $[^3H]$-TdR:

Cell cultures were incubated with 0.5 μCi (20 μl of stock solution 500 μCi/ml) per well for 6 hours at 37° C. and 5% $CO_2$. The automated cell harvester was used to lyse cells in water and adsorb the DNA onto glass-fiber filters in the format of microtiter plate. The DNA incorporated $[^3H]$-TdR was retained on the filter while unincorporated material passes through. The filters were dried at room temperature overnight, sealed into a sample bag with 10-12 ml of scintillant. The amount of $[^3H]$-TdR present in each filter (in cpm) was determined by scintillation counting in a Betaplate liquid scintillation counter. The effective dose of immunosuppressant (ED) was calculated using the following equation: ED=($CCPM_{drug\ exposed\ well}$/mean $CCPM_{control\ wells}$)×100%. The $ED_{50}$ value, the drug concentration inhibiting proliferation of 50% of lymphocytes, was calculated from the obtained dose response curves.

To evaluate immunosuppressive activity of substituted adenines, their ability to inhibit polyclonal mitogen induced proliferation of normal human lymphocytes was analyzed (Tab. 13). Our data demonstrate that these compounds have only marginal activity on $^3$H-thymidine incorporation, nonetheless, they efficiently inhibit proliferation of activated lymphocytes. Effective immunosuppressive dose of new derivatives under in vitro conditions was close to 1-20 μM.

TABLE 4

Immunosupressive activity of novel derivatives

| SUBSTITUENT R6 | Human lymphocytes $ED_{50}$ (μM) |
|---|---|
| 3-chloroanilino | 4.7 |
| 3-chloro-5-aminoanilino | 12.4 |
| 2-hydroxybenzylamino | 0.5 |
| 3-carboxy-4-chloroanilino | 2.1 |
| 3-hydroxybenzylamino | 5.6 |
| 4-bromoanilino | 4.7 |
| 4-chloroanilino | 6.2 |
| 3-amino-4-chloroanilino | 8.3 |
| 3-chloro-4-aminoanilino | 12 |
| 2-hydroxybenzylamino | 11.5 |
| 3-hydroxybenzylamino | 8.4 |
| 3-fluorobenzylamino | 18.2 |
| 3-carboxy-4-chloroanilino | 0.5 |
| 2-hydroxy-4-methoxybenzylamino | 1.8 |
| 3-chloroanilino | 7.2 |
| 2-fluorobenzylamino | 2.5 |
| 2,3-difluorobenzylamino | 10.7 |

Example 6

Inhibition of Senescence by Novel Compounds

In this example, human diploid fibroblasts (HCA cells of various passage levels: passage 25—designated HCA25; passage 45—designated HCA45; passage 80—designated HCA80) were stained for β-galactosidase activity. The medium used for cell cultivation was removed, the cells were washed twice in PNS, and fixed in 2-3 ml of fixing solution comprised of a 2% formaldehyde and 0.2% glutaraldehyde in PBS. The cells were incubated at room temperature for 5 minutes, then washed twice with PBS. The cells were subsequently incubated at 37° C. (without $CO_2$) for 1 to 16 hours in 2-3 ml of a solution comprising potassium ferricyanide (5 mM), potassium ferrocyanide (5 MM), $MgCl_2$ (2 mM), X-gal (5-bromo-4chloro-3-indolyl-β-D-galactopyranoside) (1 mg/ml), in citric/phosphate buffer, pH 6.0) Following this incubation period, the cell samples were observed in order to detect the presence of blue cells, indicating that X-gal had been cleaved (positively senescent cells). In this experiment, senescent cells, but not other cells were stained blue due to the action of β-galactosidase on the substrate (FIG. 4).

TABLE 5

The effect of Novel Compound. on Number of Senescent Cells in Culture of Human Fibroblasts

| SUBSTITUENT | SENESCENT CELLS (%) | | |
|---|---|---|---|
| R6 | HCA25 | HCA45 | HCA80 |
| CONTROL | 3 | 5 | 38 |
| 3-chloroanilino | 4 | 5 | 25 |
| 3,4-dihydroxybenzylamino | 5 | 4 | 29 |
| Anilino | 3 | 4 | 27 |
| 3-chloro-5-aminoanilino | 3 | 6 | 24 |
| 3-chloro-4-carboxyanilino | 5 | 2 | 25 |
| 3-carboxy-4-chloroanilino | 3 | 5 | 20 |
| 3-carboxy-4-hydroxyanilino | 4 | 2 | 26 |
| 4-bromoanilino | 5 | 3 | 25 |
| 4-chloroanilino | 5 | 5 | 26 |
| 3-amino-4-chloroanilino | 4 | 6 | 22 |
| 3-chloro-4-aminoanilino | 5 | 5 | 24 |
| 2-fluorobenzylamino | 4 | 3 | 16 |
| 3-fluorobenzylamino | 3 | 3 | 15 |
| 2-hydroxybenzylamino | 3 | 4 | 17 |
| 3-hydroxybenzylamino | 5 | 3 | 22 |
| 2-acetoxybenzylamino | 6 | 5 | 32 |
| 3-acetoxybenzylamino | 4 | 6 | 27 |
| 2-acetylbenzylamino | 3 | 4 | 25 |
| 3-acetylbenzylamino | 5 | 5 | 28 |
| 2-hydroxy-3-methoxybenzylamino | 4 | 3 | 20 |
| 2-hydroxy-3-methylbenzylamino | 5 | 2 | 18 |
| 2-hydroxy-3-chlorobenzylamino | 4 | 3 | 14 |
| 2,6-dihydroxy-4-chlorobenzylamino | 3 | 3 | 16 |
| 2,3-dihydroxy-4-methoxybenzylamino | 3 | 4 | 17 |
| 2,5-dihydroxy-4-methoxybenzylamino | 5 | 3 | 22 |
| 2,6-dihydroxy-4-methoxybenzylamino | 4 | 3 | 13 |
| 2,3-dihydroxy-4-chlorobenzylamino | 3 | 3 | 14 |
| 2,5-dihydroxy-4-chlorobenzylamino | 5 | 4 | 23 |
| 2-amino-6-chlorobenzylamine | 3 | 4 | 16 |
| 3-amino-4-chlorobenzylamine | 5 | 5 | 22 |
| 2,3-diamino-4-chlorobenzylamine | 4 | 3 | 17 |

As shown in Table 5 with increasing numbers of passages, the staining became darker. For the oldest cells, there were only blue cells ranging from a bright blue to an almost opaque colour. $N^6$-substituted adenine derivatives were very effective in retaining much lower level of senescent cells after 80 passages. In the case of long standing cultivation the treated cells were able to live 30% longer period than the control cells.

Example 7

Senescence Inhibition by Novel Compounds Tested on Winter Wheat Leaf Segments

Seeds of winter wheat, *Triticum aestivum* cv. Hereward, were washed under running water for 24 hours and then sown on vermiculite soaked with Knop's solution. They were placed in the grown chamber at 25° C. with a 16/8 h light period at 50 $\mu mol.m^{-2}.s^{-1}$. After 7 days, the first leaf was fully developed and the second leaf had started to grow. A tip section of the first leaf, approximately 35 mm long, was removed from 5 seedlings and trimmed slightly to a combined weight of 100 mg. The basal ends of the five leaf tips were placed in the wells of a microtiter polystyrene plate containing 150 μl of a cytokinin solution each. The entire plate was inserted into a plastic box lined with paper tissues soaked in distilled water to prevent leaf sections from drying out. After a 96 h incubation in the dark at 25° C., the leaves were removed and chlorophyll extracted by heating at 80° C. for 10 min in 5 ml of 80% ethanol (v/v). The sample volume was then restored to 5 ml by the addition of 80% ethanol (v/v). The absorbency of the extract was recorded at 665 nm. In addition, chlorophyll extracts from fresh leaves and leaf tips incubated in deionised water were measured. From the obtained data, the concentration with highest activity was selected for each compound tested. Relative activity of the compound at this concentration was calculated (Tab. 6). The activity obtained for $10^{-4}$ M 6-benzylaminopurine (BAP) was postulated as 100%. The values shown are means of five replicates and the whole experiment was repeated twice. The cytokinins to be tested were dissolved in dimethylsulfoxide (DMSO) and the solution brought up to $10^{-3}$M with distilled water. This stock was further diluted in distilled water to concentrations ranging from $10^{-8}$M to $10^{-4}$M. The final concentration of DMSO did not exceed 0.2% and therefore did not affect biological activity in the assay system used.

TABLE 6

Effect of new cytokinin derivatives on retention of chlorophyll in excised wheat leaf tips. Standard deviations are of the mean for 10 replicate determination

| Tested compound | concentration with highest activity (mol. $l^{-1}$) | Activity (%) [$10^{-4}$ mol. $l^{-1}$ BAP = 100%] |
|---|---|---|
| 1. 6-(2-fluorobenzylamino)purine | $10^{-4}$ | 169 (±20) |
| 2. 6-(3-fluorobenzylamino)purine | $10^{-4}$ | 200 (±25) |
| 3. 6-(4-fluorobenzylamino)purine | $10^{-4}$ | 95.5 (±3.5) |
| 4. 6-(2-chlorobenzylamino)purine | $10^{-4}$ | 116.5 (±6.5) |
| 5. 6-(3-chlorobenzylamino)purine | $10^{-4}$ | 82 (±2) |

TABLE 6-continued

Effect of new cytokinin derivatives on retention of chlorophyll in excised wheat leaf tips. Standard deviations are of the mean for 10 replicate determination

| Tested compound | concentration with highest activity (mol. $l^{-1}$) | Activity (%) [$10^{-4}$ mol. $l^{-1}$ BAP = 100%] |
|---|---|---|
| 6. 6-(4-chlorobenzylamino)purine | $10^{-4}$ | 64.5 (±13.5) |
| 7. 6-(2-bromobenzylamino)purine | $10^{-4}$ | 52 (±14) |
| 8. 6-(3-bromobenzylamino)purine | $10^{-4}$ | 48 (±6) |
| 9. 6-(4-bromobenzylamino)purine | $10^{-5}$ | 30 (±15) |
| 10. 6-(3-iodobenzylamino)purine | $10^{-4}$ | 83.5 (±23) |
| 11. 6-(2-methylbenzylamino)purine | $10^{-4}$ | 158 (±29) |
| 12. 6-(3-methylbenzylamino)purine | $10^{-4}$ | 111 (±16) |
| 13. 6-(4-methylbenzylamino)purine | $10^{-4}$ | 35 (±23) |
| 14. 6-(2-methoxybenzylamino)purine | $10^{-4}$ | 269 (±12) |
| 15. 6-(3-methoxybenzylamino)purine | $10^{-4}$ | 178 (±16) |
| 16. 6-(4-methoxybenzylamino)purine | $10^{-4}$ | 79 (±6) |
| 17. 6-(3-nitrobenzylamino)purine | $10^{-4}$ | 60 (±15) |
| 18. 6-(4-nitrobenzylamino)purine | $10^{-4}$ | 83 (±8) |
| 19. 6-(2,4-dichlorbenzylamino)purine | $10^{-5}$ | 0 |
| 20. 6-(3,4-dichlorbenzylamino)purine | $10^{-4}$ | 117 (±22) |
| 21. 6-(2,3-dimethoxybenzylamino)purine | $10^{-4}$ | 109 (±5) |
| 22. 6-(2,4-dimethoxybenzylamino)purine | $10^{-7}$ | 26 (±11) |
| 23. 6-(3,4-dimethoxybenzylamino)purine | $10^{-4}$ | 43 (±17) |
| 24. 6-(3,5-dimethoxybenzylamino)purine | $10^{-4}$ | 16 (±1) |
| 25. 2-amino-6-(3-hydroxybenzylamino)purine | $10^{-4}$ | 121 (±7) |
| 26. 2-chlor-6-(3-hydroxybenzylamino)purine | $10^{-4}$ | 140 (±13) |
| 27. 2-methylthio-6-(3-hydroxybenzylamino)purine | $10^{-4}$ | 50.5 (±23.5) |
| 28. 6-(2,4,6-trimethoxybenzylamino)purine | $10^{-4}$ | 6 (±4) |
| 29. 6-(3,4,5-trimethoxybenzylamino)purine | $10^{-4}$ | 25 (±2) |
| 30. 6-(2,4-difluorobenzylamino)purine | $10^{-5}$ | 139 (±2) |
| 31. 6-(3,5-difluorobenzylamino)purine | $10^{-5}$ | 156 (±4) |
| 32. 6-(2,3,4-trifluorobenzylamino)purine | $10^{-5}$ | 131 (±22) |
| 33. 6-(3-chloro-4-fluorobenzylamino)purine | $10^{-5}$ | 141 (±20) |
| 33. 6-(2-hydroxy-3-methoxybenzylamino)purine | $10^{-5}$ | 34 (±5) |

Example 8

Stimulation Effect of the New Compounds on Plant Cell Division

Cytokinin-dependent tobacco callus *Nicotiana tabacum* L. cv. Wisconsin 38 was maintained at 25° C. in darkness on modified Murashige-Skoog medium, containing per 1 liter: 4 μmol nicotinic acid, 2.4 μmol pyridoxine hydrochloride, 1.2 μmol thiamine, 26.6 μmol glycine, 1.37 μmol glutamine, 1.8 μmol myo-inositol, 30 g of sucrose, 8 g of agar, 5.37 μmol α-naphtylacetic acid (NAA) and 0.5 μmol benzylaminopurine (BAP). Subcultivation was carried out every three weeks. Fourteen days before the bioassay, the callus tissue was transferred to the media without 6-benzylaminopurine (BAP). Biological activity was determined from the increase in fresh callus weight after four weeks of cultivation. Five replicates were prepared for each cytokinin concentration and the entire test was repeated twice. From the obtained data, the concentration with highest activity was selected for each compound tested. Relative activity of the compound at this concentration was calculated (Tab. 6). The activity obtained for $10^{-4}$ M 6-benzylaminopurine (BAP) was postulated as 100%. The cytokinins to be tested were dissolved in dimethylsulfoxide (DMSO) and the solution brought up to $10^{-3}$M with distilled water. This stock was further diluted in the respective media used for the biotest to concentrations ranging from $10^{-8}$M to $10^{-4}$M. The final concentration of DMSO did not exceed 0.2% and therefore did not affect biological activity in the assay system used.

TABLE 7

The effect of new cytokinin derivatives on growth of cytokinin-dependent tobacco callus *Nicotiana tabacum* L. cv. Wisconsins 38

| Tested compound | Concentration with highest activity (mol. $l^{-1}$) | activity (%) [$10^{-5}$ mol. $l^{-1}$ BAP = 100%] |
|---|---|---|
| 1. 6-(2-fluorobenzylamino)purine | $10^{-6}$ | 111 (±21) |
| 2. 6-(3-fluorobenzylamino)purine | $10^{-5}$ | 135 (±8) |

TABLE 7-continued

The effect of new cytokinin derivatives on growth of cytokinin-dependent tobacco callus *Nicotiana tabacum* L. cv. Wisconsins 38

| Tested compound | Concentration with highest activity (mol. l$^{-1}$) | activity (%) [10$^{-5}$ mol. l$^{-1}$ BAP = 100%] |
|---|---|---|
| 3. 6-(4-fluorobenzylamino)purine | 10$^{-6}$ | 122 (±12) |
| 4. 6-(2-chlorobenzylamino)purine | 10$^{-6}$ | 93 (±4) |
| 5. 6-(3-chlorobenzylamino)purine | 10$^{-5}$ | 94 (±6) |
| 6. 6-(4-chlorobenzylamino)purine | 10$^{-6}$ | 64 (±8) |
| 7. 6-(2-bromobenzylamino)purine | 10$^{-5}$ | 102 (±5) |
| 8. 6-(3-bromobenzylamino)purine | 10$^{-6}$ | 85 (±11) |
| 9. 6-(4-bromobenzylamino)purine | 10$^{-6}$ | 15 (±9) |
| 10. 6-(3-iodobenzylamino)purine | 10$^{-5}$ | 76 (±8) |
| 11. 6-(2-methylbenzylamino)purine | 10$^{-6}$ | 118 (±3) |
| 12. 6-(3-methylbenzylamino)purine | 10$^{-6}$ | 79 (±5) |
| 13. 6-(4-methylbenzylamino)purine | 10$^{-6}$ | 52 (±8) |
| 14. 6-(2-methoxybenzylamino)purine | 10$^{-5}$ | 79 (±5) |
| 15. 6-(3-methoxybenzylamino)purine | 10$^{-6}$ | 76 (±20) |
| 16. 6-(4-methoxybenzylamino)purine | 10$^{-6}$ | 39 (±17) |
| 17. 6-(2,4-dichlorobenzylamino)purine | 10$^{-4}$ | 11 (±3) |
| 18. 6-(3,4-dichlorobenzylamino)purine | 10$^{-4}$ | 45 (±7) |
| 19. 6-(2,3-dimethoxybenzylamino)purine | 10$^{-5}$ | 8.5 (±2) |
| 20. 6-(2,4-dimethoxybenzylamino)purine | 10$^{-5}$ | 21 (±5) |
| 21. 6-(2,4,6-trimethoxybenzylamino)purine | 10$^{-4}$ | 13 (±6) |
| 22. 6-(3,4,5-trimethoxybenzylamino)purine | 10$^{-5}$ | 19 (±3) |
| 23. 6-(3,4-dihydroxybenzylamino)purine | 10$^{-5}$ | 4 (±1) |
| 24. 6-(2,4-difluorobenzylamino)purine | 10$^{-5}$ | 95 (±1) |
| 25. 6-(3,5-difluorobenzylamino)purine | 10$^{-5}$ | 97 (±3) |
| 26. 6-(2,3,4-trifluorobenzylamino)purine | 10$^{-5}$ | 76 (±4) |
| 27. 6-(3-chloro-4-fluorobenzylamino)purine | 10$^{-5}$ | 90 (±1) |

Example 9

Testing of Novel Compounds in *Amaranthus* Bioassay

Standard *Amaranthus* bioassay was performed with several modifications. The seeds of *Amaranthus caudatus* var. *atropurpurea* were surface-sterilised in 10% N-chlorobenzenesulfonamide (w/v) for 10 min and washed 5 times in deionized water. They were placed in 14 cm Petri dishes containing paper tissues saturated with deionized water. After 72 h of cultivation at 25° C. in darkness, the roots of the seedlings were cut off. The explants, consisting of two cotyledons and hypocotyls, were placed in 5 cm Petri dishes on two layers of filter paper soaked in 1 ml of incubation medium containing 10 μmol NA$_2$HPO$_4$—KH$_2$PO$_4$, pH 6.8, 5 μmol tyrosine and the cytokinin to be tested. There were 20 explants per dish. The procedure was carried out under a green safe light in a darkroom. After a 48 h of incubation at 25° C. in darkness, betacyanin was extracted by freezing the explants in 4 ml 3.33 μM acetic acid. The concentration of betacyanin was determined by comparing the absorbance at 537 nm and 620 nm as follows: $\Delta A = A_{537nm} - A_{620nm}$. From the obtained data, the concentration with highest activity was selected for each compound tested. Relative activity of the compound at this concentration was calculated (Tab. 6). The activity obtained for 10$^{-4}$ M 6-benzylaminopurine (BAP) was postulated as 100%. The values shown in table 8 are means of five replicates and the entire test was repeated twice.

The cytokinins to be tested were dissolved in dimethylsulfoxide (DMSO) and the solution brought up to 10$^{-3}$M with distilled water. This stock was further diluted in the respective media used for the biotest to concentrations ranging from 10$^{-8}$M to 10$^{-4}$M. The final concentration of DMSO did not exceed 0.2% and therefore did not affect biological activity in the assay system used.

TABLE 8

The effect of new cytokinin derivatives on betacyanin content in *Amaranthus caudatus* cotyledon/hypocotyl explants.

| Compound | Concentration with highest Activity (mol. l$^{-1}$) | activity (%) [10$^{-5}$mol. l$^{-1}$ BAP = 100%] |
|---|---|---|
| 1. 6-(2-fluorobenzylamino)purine | 10$^{-4}$ | 116 (±3) |
| 2. 6-(3-fluorobenzylamino)purine | 10$^{-4}$ | 140 (±5) |
| 3. 6-(4-fluorobenzylamino)purine | 10$^{-5}$ | 44 (±4) |
| 4. 6-(2-chlorobenzylamino)purine | 10$^{-5}$ | 109 (±8) |
| 5. 6-(3-chlorobenzylamino)purine | 10$^{-5}$ | 96 (±5) |
| 6. 6-(4-chlorobenzylamino)purine | 10$^{-5}$ | 35 (±7) |
| 7. 6-(2-bromobenzylamino)purine | 10$^{-4}$ | 94 (±6) |
| 8. 6-(3-bromobenzylamino)purine | 10$^{-4}$ | 71 (±5) |

TABLE 8-continued

The effect of new cytokinin derivatives on betacyanin content in *Amaranthus caudatus* cotyledon/hypocotyl explants.

| Compound | Concentration with highest Activity (mol. $l^{-1}$) | activity (%) [$10^{-5}$mol. $l^{-1}$ BAP = 100%] |
|---|---|---|
| 9. 6-(4-bromobenzylamino)purine | $10^{-5}$ | 17 (±7) |
| 10. 6-(3-iodobenzylamino)purine | $10^{-5}$ | 79 (±3) |
| 11. 6-(2-methylbenzylamino)purine | $10^{-5}$ | 98 (±22) |
| 12. 6-(3-methylbenzylamino)purine | $10^{-5}$ | 84 (±14) |
| 13. 6-(4-methylbenzylamino)purine | $10^{-5}$ | 26 (±10) |
| 14. 6-(2-methoxybenzylamino)purine | $10^{-5}$ | 77 (±5) |
| 15. 6-(3-methoxybenzylamino)purine | $10^{-4}$ | 90 (±16) |
| 16. 6-(4-methoxybenzylamino)purine | $10^{-4}$ | 23 (±2) |
| 17. 6-(3-nitrobenzylamino)purine | $10^{-4}$ | 66 (±7) |
| 18. 6-(4-nitrobenzylamino)purine | $10^{-4}$ | 25 (±2) |
| 19. 6-(2,4-dichlorobenzylamino)purine | $10^{-4}$ | 19 (±8) |
| 20. 6-(3,4-dichlorobenzylamino)purine | $10^{-4}$ | 63 (±10) |
| 21. 6-(2,3-dimethoxybenzylamino)purine | $10^{-4}$ | 22 (±3) |
| 22. 6-(2,4-dimethoxybenzylamino)purine | $10^{-5}$ | 12 (±2) |
| 23. 6-(3,4-dimethoxybenzylamino)purine | $10^{-4}$ | 27 (±6) |
| 24. 6-(3,5-dimethoxybenzylamino)purine | $10^{-4}$ | 1.5 (±1) |
| 25. 6-(2,4,6-trimethoxybenzylamino)purine | $10^{-4}$ | 3 (±3) |
| 26. 6-(3,4,5-trimethoxybenzylamino)purine | $10^{-4}$ | 2 (±2) |
| 27. 6-(3,4-dihydroxybenzylamino)purine | $10^{-4}$ | 8 (±3) |
| 28. 6-(2,4-difluorobenzylamino)purine | $10^{-4}$ | 88 (±7) |
| 29. 6-(3,5-difluorobenzylamino)purine | $10^{-4}$ | 108 (±2) |
| 30. 6-(2,3,4-trifluorobenzylamino)purine | $10^{-4}$ | 94 (±3) |
| 31. 6-(3-chloro-4-fluorobenzylamino)purine | $10^{-4}$ | 91 (±7) |
| 32. 6-(2-hydroxy-3-methoxybenzylamino)purine | $10^{-4}$ | 19 (±3) |
| 33. 6-(3-hydroxy-4-methoxybenzylamino)purine | $10^{-4}$ | 24 (±1) |
| 34. 6-(4-hydroxy-3-methoxybenzylamino)purine | $10^{-4}$ | 10 (±2) |

Example 10

The Effect of New Derivatives on in vitro and post vitro Multiplication and Rooting of Rose (*Rosa multiflora*)

The aim of this experiment was to test whether the new compounds are of practical use in tissue culture practice. The multiplication rate was investigated and the post vitro effects on rooting were examined. *Rosa hybrida* (pot rose cultivar) was cultured in 350 ml vessels with a screw on polycarbonate lid. Each culture vessel contained 100 ml autoclaved medium (120° C., 20 min). The cultures were maintained at 23±2° C. under a 16 h photoperiod at 40 μM $m^{-2}$ $s^{-1}$ PAR. The basal medium (BMR) contained Murashige and Skoog (1962) macroelements, microelements and vitamins, 95 μM NaFeEDTA, 555 μM myo-inositol, 111 mM sucrose, 1.332 mM glycine, 684 μM L-glutamine and 7 g/l agar. This medium was supplemented with 10 μM BA, mT, oMeOBAP or mMeOBAP (compound no. 14 and 15, respectively). The control medium didn't contain any cytokinin. After a culture period of 8 weeks, the number of induced shoots per explant was determined, as well as root number/explant and total root length/explant. The roots were removed and the explants (shoot clusters) were planted in unfertilised peat. After four weeks of acclimatising in a fog unit, root number and root length was determined.

As expected, a cytokinin free medium yielded almost no new shoots. The original shoot explant grew out as a good quality single shoot that rooted very well. BAP gave a high shoot multiplication rate, but the shoots rooted badly. The new BAP derivatives tested, induced formation of new shoots and rooting significantly better, when compared with BAP itself (Tab. 9).

TABLE 9

Effects of cytokinins on in vitro and post vitro shoot multiplication and rooting in *Rosa multiflora*

| | In vitro | | | | Ex vitro | |
|---|---|---|---|---|---|---|
| Cytokinin | Number of new shoots per explant | Flower number per explant | Root number per explant | Total root length per explant (cm) | Root number per plant | Total root length per plant (cm) |
| 0 | 0.2 | 0.03 | 0.8 | 1.2 | 4.6 | 17.1 |

TABLE 9-continued

Effects of cytokinins on in vitro and post vitro shoot multiplication and rooting in Rosa multiflora

| | In vitro | | | | Ex vitro | |
|---|---|---|---|---|---|---|
| Cytokinin | Number of new shoots per explant | Flower number per explant | Root number per explant | Total root length per explant (cm) | Root number per plant | Total root length per plant (cm) |
| BA* | 3.8 | 0.00 | 0.0 | 0.0 | 0.6 | 1.1 |
| MOHBAP | 2.1 | 0.16 | 0.0 | 0.0 | 1.4 | 3.8 |
| OmeOBAP | 1.0 | 0.29 | 0.0 | 0.0 | 2.5 | 8.5 |
| MmeOBAP | 4.3 | 0.03 | 0.0 | 0.0 | 1.7 | 4.1 |

*BA = benzylamino

Example 11

Early Shoot Senescence Inhibition of Tissue Cultured Roses (Rosa hybrida)

Tissue cultured roses suffer from senescence symptoms. The leafs start to turn brown and after some weeks all explants in a vessel die off. The symptoms start earlier when the aeration of the vessel is inhibited, for instance by a plastic foil. This suggests that ethylene our other gaseous components are involved. The cytokinins which are applied to the medium, induce ethylene, so it looked worthwhile to test the promising new cytokinin compounds on this system.

Rosa hybrida 'Pailin' (a cut rose) was cultured in 350 ml vessels with a screw on polycarbonate lid. Each culture vessel contained 100 ml autoclaved medium (120° C., 20 min). The cultures were maintained at 23±2° C. under a 16 h photoperiod at 40 µM m$^{-2}$ s$^{-1}$ PAR. The basal medium (BMR) contained Murashige and Skoog (1962) macroelements, microelements and vitamins, 36.7 mg/l NaFeEDTA, 50 mg/l NaFeEDDHA, 100 mg/l µM myo-inositol, 30 g/l sucrose, 100 mg/l glycine, 50 mg/l calcium pantothenate, 100 mg/l L-glutamine and 7 g/l agar-agar. This medium was supplemented with 10 µM BA, mT and mMeOBAP. The last 2 cytokinins were filter sterilised and added after autoclaving the medium in the vessels. The control medium didn't contain any cytokinin. After a culture period of 6 weeks, scoring senescence symptoms was started. The day on which the first brown leaf appeared was noted for each plant (FIG. 8), as well as the day of complete dying of the whole explant (FIG. 9, 10).

On medium with BA, the relative number of dead plants looks like a sigmoid curve, suggesting an autocatalytic senescence effect, maybe caused by ethylene. It would be interesting to measure the ethylene concentration in the headspace. On mT and mMeOBAP the situation improved. mMeOBAP was definitely the best compound. Even after 121 days almost all plants were still alive. Although some brown leaves could not be avoided on a medium with mMeOBAP, these plants could be easily used for a next subculture. The use of mMeOBAP is a significant improvement in the micropropagation of roses (Rosa hybrida).

Example 12

Dry Capsules 5000 capsules, each of which contains 0.25 g of one of the compounds of the formula I, II and III mentioned in the preceding or following Examples as active ingredient, are prepared as follows:

| Composition | |
|---|---|
| Active ingredient | 1250 g |
| Talc | 180 g |
| Wheat starch | 120 g |
| Magnesium stearate | 80 g |
| Lactose | 20 g |

Preparation process: The powdered substances mentioned are pressed through a sieve of mesh width 0.6 mm. Portions of 0.33 g of the mixture are transferred to gelatine capsules with the aid of a capsule-filling machine.

Example 13

Soft Capsules 5000 soft gelatine capsules, each of which contains 0.05 g of one of the compounds of the formula I, II and III mentioned in the preceding or following Examples as active ingredient, are prepared as follows:

| Composition | |
|---|---|
| Active ingredient | 250 g |
| Lauroglycol | 2 litres |

Preparation process: The powdered active ingredient is suspended in Lauroglykol® (propylene glycol laurate, Gattefossé S.A., Saint Priest, France) and ground in a wet-pulveriser to a particle size of about 1 to 3 µm. Portions of in each case 0.419 g of the mixture are then transferred to soft gelatine capsules by means of a capsule-filling machine.

Example 14

Soft Capsules 5000 soft gelatine capsules, each of which contain 0.05 g of one of the compounds of the formula I, II or III mentioned in the preceding or following Examples as active ingredient, are prepared as follows:

| Composition | |
|---|---|
| Active ingredient | 250 g |
| PEG 400 | 1 litre |
| Tween 80 | 1 litre |

Preparation process: The powdered active ingredient is suspended in PEG 400 (polyethylene glycol of Mw between 380 and about 420, Sigma, Fluka, Aldrich, USA) and Tween® 80 (polyoxyethylene sorbitan monolaurate, Atlas Chem. Inc., Inc., USA, supplied by Sigma, Fluka, Aldrich, USA) and ground in a wet-pulveriser to a particle size of about 1 to 3 mm. Portions of in each case 0.43 g of the mixture are then transferred to soft gelatine capsules by means of a capsule-filling machine.

INDUSTRIAL APPLICABILITY

The new heterocyclic compounds based on $N^6$-substituted adenine according to the invention are useful in diagnostic and therapeutic method especially in the pharmaceutical industry, in cosmetics, in biotechnology and in agriculture.

The invention claimed is:

1. An ageing- and senescence-inhibiting cosmetic composition comprising a heterocyclic compound based on N6-substituted adenine of the formula I

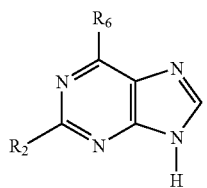

and the pharmaceutically acceptable salts thereof, wherein
R2 is hydrogen,
R6 is R6'-X,
wherein X is —NH—;
R6' is substituted phenyl or substituted benzyl,
whereas the generic substituent groups have meanings identical with the definitions of the corresponding groups as defined in this legend, wherein
"substituted phenyl" refers to phenyl group which is substituted with one to five hydroxy and alkoxy groups, one to five hydroxy and halogen groups, one to five hydroxy and alkyl groups or one to five amino and halogen groups as defined herein,
"substituted benzyl" refers to the phenylmethyl group, wherein the phenyl group is substituted with one to five hydroxy and alkoxy groups, one to five hydroxy and halogen groups, one to five hydroxy and alkyl groups or one to five amino and halogen groups as defined herein,
whereas the generic substituent groups have meanings identical with the definitions of the corresponding groups as defined in this legend, wherein
"halogen" refers to fluorine, bromine, chlorine and iodine atoms;
"hydroxyl" refers to the group —OH;
"alkyl" refers to branched or unbranched $C_1$-$C_6$ saturated chain being selected from the group consisting of methyl, propyl, isopropyl, tert-butyl;
"alkoxy" denotes the group —OR, wherein R is alkyl as defined herein;
and the racemates, optical isomers or acid salts thereof, including a pharmaceutical carrier.

2. An ageing- and senescence-inhibiting cosmetic composition which contains a heterocyclic compound based on $N^6$-substituted adenine of the formula I according to claim 1 wherein the compound is selected from 6-(2-hydroxy-4-chlorobenzylamino)purine, 6-(2-hydroxy-5-chlorobenzylamino)purine, 6-(2-hydroxy-6-chlorobenzylamino)purine, 6-(2,3-dihydroxy-4-methoxybenzylamino)purine, 6-(2,5-dihydroxy-4-methoxybenzylamino)purine, 6-(2,6-dihydroxy-3-methoxybenzylamino)purine, 6-(2,5-dihydroxy-3-methoxybenzylamino)purine, 6-(2,6-dihydroxy-4-methoxybenzylamino)purine, 6-(2,3-dihydroxy-4-chlorobenzylamino)purine, 6-(2,5-dihydroxy-4-chlorobenzylamino)purine, 6-(2,6-dihydroxy-4-chlorobenzylamino)purine, 6-(2,6-dihydroxy-3-chlorobenzylamino)purine, 6-(3-hydroxy-4-methoxybenzylamino)purine, 6-(2-hydroxy-3-methoxybenzylamino)purine, 6-(4-hydroxy-3-methoxybenzylamino)purine, 6-(2-hydroxy-4-methoxybenzylamino)purine, 6-(4-hydroxy-2-methoxybenzylamino)purine, 6-(2-hydroxy-5-methoxybenzylamino)purine, 6-(3-hydroxy-4-methoxybenzylamino)purine, 6-(4-hydroxy-3-methoxybenzylamino)purine, 6-(2-hydroxy-6-methoxybenzylamino)purine, 6-(3-hydroxy-5-methoxybenzylamino)purine, 6-(2,6-dimethyl-4-hydroxybenzylamino)purine, 6-(3,5-dimethyl-4-hydroxybenzylamino)purine, 6-(2-amino-6-chlorobenzylamino)purine, 6-(3-amino-4-chlorobenzylamino)purine, 6-(2-amino-3-chlorobenzylamino)purine, 6-(2-amino-4-chlorobenzylamino)purine, 6-(2-amino-6-chlorobenzylamino)purine, 6-(2,6-diamino-3-chlorobenzylamino)purine, 6-(2,6-diamino-4-chlorobenzylamino)purine, 6-(4-amino-3-chlorobenzylamino)purine, 6-(4-hydroxy-2-methylanilino)purine, 6-(5-chloro-2-hydroxyanilino)purine, 6-(3-chloro-5-aminoanilino)purine, 6-(3-amino-4-chloroanilino)purine, 6-(3-chloro-4-aminoanilino)purine, including a pharmaceutical carrier.

3. A method for inhibiting ageing and senescence of mammalian epidermal cells, said method comprising administering to a mammal in need of such treatment an ageing- and senescence-inhibiting cosmetic composition comprising a heterocyclic compound based on N6-substituted adenine of the formula I

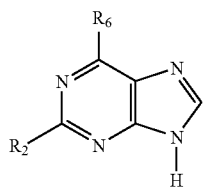

and the pharmaceutically acceptable salts thereof, wherein
R2 is hydrogen,
R6 is R6'-X,
wherein X is —NH—;
R6' is substituted phenyl or substituted benzyl,
whereas the generic substituent groups have meanings identical with the definitions of the corresponding groups as defined in this legend, wherein
"substituted phenyl" refers to phenyl group which is substituted with one to five hydroxy and alkoxy groups, one to five hydroxy and halogen groups, one to five hydroxy and alkyl groups or one to five amino and halogen groups as defined herein,
"substituted benzyl" refers to the phenylmethyl group, wherein the phenyl group is substituted with one to five hydroxy and alkoxy groups, one to five hydroxy and halogen groups, one to five hydroxy and alkyl groups or one to five amino and halogen groups as defined herein,
whereas the generic substituent groups have meanings identical with the definitions of the corresponding groups as defined in this legend, wherein
"halogen" refers to fluorine, bromine, chlorine and iodine atoms;
"hydroxyl" refers to the group —OH;
"alkyl" refers to branched or unbranched $C_1$-C6 saturated chain being selected from the group consisting of methyl, propyl, isopropyl, tert-butyl;
"alkoxy" denotes the group —OR, wherein R is alkyl as defined herein;
and the racemates, optical isomers or acid salts thereof, including a pharmaceutical carrier.

4. A method for inhibiting ageing and senescence of mammalian epidermal cells, said method comprising administering to a mammal in need of such treatment an ageing- and senescence-inhibiting cosmetic composition comprising a compound selected from 6-(2-hydroxy-4-chlorobenzylamino)purine, 6-(2-hydroxy-5-chlorobenzylamino)purine, 6-(2-hydroxy-6-chlorobenzylamino)purine, 6-(2,3-dihydroxy-4-methoxybenzylamino)purine, 6-(2,5-dihydroxy-4-methoxybenzylamino)purine, 6-(2,6-dihydroxy-3-methoxybenzylamino)purine, 6-(2,5-dihydroxy-3-methoxybenzylamino)purine, 6-(2,6-dihydroxy-4-methoxybenzylamino)purine, 6-(2,3-dihydroxy-4-chlorobenzylamino)purine, 6-(2,5-dihydroxy-4-chlorobenzylamino)purine, 6-(2,6-dihydroxy-4-chlorobenzylamino)purine, 6-(2,6-dihydroxy-3-chlorobenzylamino)purine, 6-(3-hydroxy-4-methoxybenzylamino)purine, 6-(2-hydroxy-3-methoxybenzylamino)purine, 6-(4-hydroxy-3-methoxybenzylamino)purine, 6-(2-hydroxy-4-methoxybenzylamino)purine, 6-(4-hydroxy-2-methoxybenzylamino)purine, 6-(2-hydroxy-5-methoxybenzylamino)purine, 6-(3-hydroxy-4-methoxybenzylamino)purine, 6-(4-hydroxy-3-methoxybenzylamino)purine, 6-(2-hydroxy-6-methoxybenzylamino)purine, 6-(3-hydroxy-5-methoxybenzylamino)purine, 6-(2,6-dimethyl-4-hydroxybenzylamino)purine, 6-(3,5-dimethyl-4-hydroxybenzylamino)purine, 6-(2-amino-6-chlorobenzylamino)purine, 6-(3-amino-4-chlorobenzylamino)purine, 6-(2-amino-3-chlorobenzylamino)purine, 6-(2-amino-4-chlorobenzylamino)purine, 6-(2-amino-6-chlorobenzylamino)purine, 6-(2,6-diamino-3-chlorobenzylamino)purine, 6-(2,6-diamino-4-chlorobenzylamino)purine, 6-(4-amino-3-chlorobenzylamino)purine, 6-(4-hydroxy-2-methylanilino)purine, 6-(5-chloro-2-hydroxyanilino)purine, 6-(3-chloro-5-aminoanilino)purine, 6-(3-amino-4-chloroanilino)purine, 6-(3-chloro-4-aminoanilino)purine, including a pharmaceutical carrier.

5. A method of claim 3, wherein the mammalian epidermal cells are fibroblasts.

6. A method of claim 4, wherein the mammalian epidermal cells are fibroblasts.

* * * * *